(12) United States Patent
Shiozawa et al.

(10) Patent No.: US 7,741,030 B2
(45) Date of Patent: Jun. 22, 2010

(54) METHODS FOR DIAGNOSING RHEUMATOID ARTHRITIS

(75) Inventors: Shunichi Shiozawa, 11-6. Takenodai 2-chome, Nishi-ku, Kobe-shi, Hyogo (JP) 651-2274; Kayo Osawa, Kobe (JP); Nozomi Takami, Kobe (JP); Akira Hashiramoto, Kobe (JP); Yasushi Miura, Kobe (JP)

(73) Assignee: Shunichi Shiozawa, Kobe-shi, Hyogo (JP)

( * ) Notice: Subject to any disclaimer, the term of this patent is extended or adjusted under 35 U.S.C. 154(b) by 515 days.

(21) Appl. No.: 10/590,823

(22) PCT Filed: Nov. 25, 2004

(86) PCT No.: PCT/JP2004/017497

§ 371 (c)(1),
(2), (4) Date: Nov. 21, 2007

(87) PCT Pub. No.: WO2005/083071

PCT Pub. Date: Sep. 9, 2005

(65) Prior Publication Data

US 2009/0035752 A1    Feb. 5, 2009

(30) Foreign Application Priority Data

Feb. 26, 2004  (JP) .............. 2004-052495
Apr. 6, 2004   (JP) .............. 2004-112548
Aug. 26, 2004  (JP) .............. 2004-247525
Oct. 12, 2004  (JP) .............. 2004-297965

(51) Int. Cl.
C12Q 1/68    (2006.01)
C12P 19/34   (2006.01)
C07H 21/02   (2006.01)
C07H 21/04   (2006.01)

(52) U.S. Cl. .............. 435/6; 435/91.2; 536/23.1; 536/24.1; 536/24.31

(58) Field of Classification Search .............. None
See application file for complete search history.

(56) References Cited

U.S. PATENT DOCUMENTS 6,623,924 B1    9/2003    Shiozawa

FOREIGN PATENT DOCUMENTS

| JP | 10-513257 A | 12/1998 |
| WO | WO96/20213 A1 | 7/1996 |
| WO | WO98/51791 A1 | 11/1998 |
| WO | 01/32921 A2 | 5/2001 |
| WO | 02/34912 A1 | 5/2002 |

OTHER PUBLICATIONS

Ehrlich et al. Oncogene 2002. 21: 5400-5413.*
Takami et al. Arthritis and Rheumatism. Sep. 2004. 50, p. S671, Abstract 1796.*
Muller-Tidow et al. FEBS Letters. 2001. 490: 75-78.*
Sato et al (Arthritis and Rheumatism. Sep. 2003. S458, Abstract 1146.*
Hitoshi Ishikawa, "Guidelines for the Diagnosis of Chronic Rheumatoid Arthritis"; Treatment, vol. 73, No. 3, 1991, pp. 23-27.
Susan J. Clark et al.; "High Sensitivity mapping of Methylated Cytosines"; Nucleic Acid Research, vol. 22, No. 15, 1994, pp. 2990-2997.
James G. Herman et al.; "Methylation-Specific PCT: A novel PCR Assay for Methylation Status of CpG Islands" (DNA methylation/tumor suppressor genes/p16/p15); Proc. Natl. Acad. Sci. USA, vol. 93, 1996, pp. 9821-9826.
Akira Hashiramoto et al.; "C-MYC Antisense Oligodeoxynucleotides can Induce Apoptosis and Down-Regulate Fas Expression in Rheumatoid Synoviocytes"; Arthritis & Rheumatism, vol. 42, No. 5, May 1999, pp. 954-962.
Satoshi Miyazaki et al.; "ACTH Expression in Synovium of Patients with Rheumatoid Arthritis and Lewis Rats with Adjuvant Arthritis"; Mod Rheumatol, 12, 2002, pp. 206-212.
Tadashi Yamashita et al.; "Enhanced Insulin Sensitivity in Mice Lacking Ganglioside GM3"; PNAS, vol. 100, No. 6, Mar. 2003, pp. 3445-3449.
Rieder et al. "*Homo sapiens* tumor necrosis factor receptor superfamily, member 25 (TNFRSF25) gene, complete cds" NCBI GenBank Accession No. AY254324 (2003).
Office Action for Canadian Appln. No. 2,557,368 dated Feb. 10, 2009.
International Search Report of PCT/JP2004/017497, mailed Feb. 22, 2005.
Takami, "Dai 1 Senshokutaijo ni Sonzaisuru RA no Shikkan Idenshi DR3 no Genom Imprinting no Kansuru Kenkyu", Dai 26 Kai The Molecular Biology Society of Japan Nekai Program, Nov. 25, 2003, p. 1035.

* cited by examiner

*Primary Examiner*—Carla Myers
(74) *Attorney, Agent, or Firm*—Nixon & Vanderhye P.C.

(57) ABSTRACT

Analysis is made on the DNA methylation of the region (including a promoter region) upstream from the translation initiation point of a rheumatoid arthritis-associated gene DR3 in human genome. As a result, it is found out that an allele-specific methylation occurs in a CpG sequence located about −380 to −180 bp upstream from translation initiation point (ATG) of the gene DR3. It is further found out that the CpG sequences downstream therefrom of the genes DR3 originating in healthy subjects are all in the unmethylated state, while methylated and unmethylated sequences are both observed in the genes DR3 originating in RA patients.

6 Claims, 16 Drawing Sheets

FIG. 5 (a)
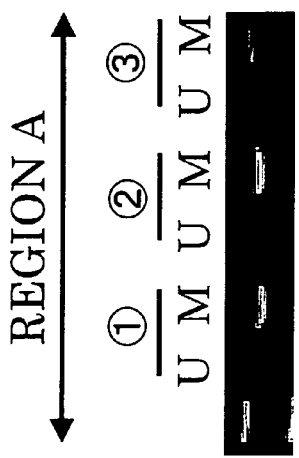

REGION A

① ② ③
U M U M U M

U: UNMETHYLATION-SPECIFIC PRIMERS
M: METHYLATION-SPECIFIC PRIMERS
①: SINOVIAL CELL DNA
②: SINOVIAL INFILTRATIVE LYMPHOCYTE DNA
③: JOINT FLUID LYMPHOCYTE DNA

FIG. 5 (b)
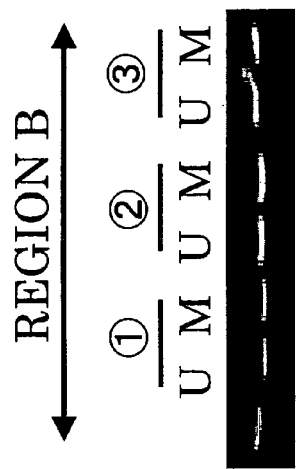

REGION B

① ② ③
U M U M U M

U: UNMETHYLATION-SPECIFIC PRIMERS
M: METHYLATION-SPECIFIC PRIMERS
①: SINOVIAL CELL DNA
②: SINOVIAL INFILTRATIVE LYMPHOCYTE DNA
③: JOINT FLUID LYMPHOCYTE DNA

FIG. 5 (c)
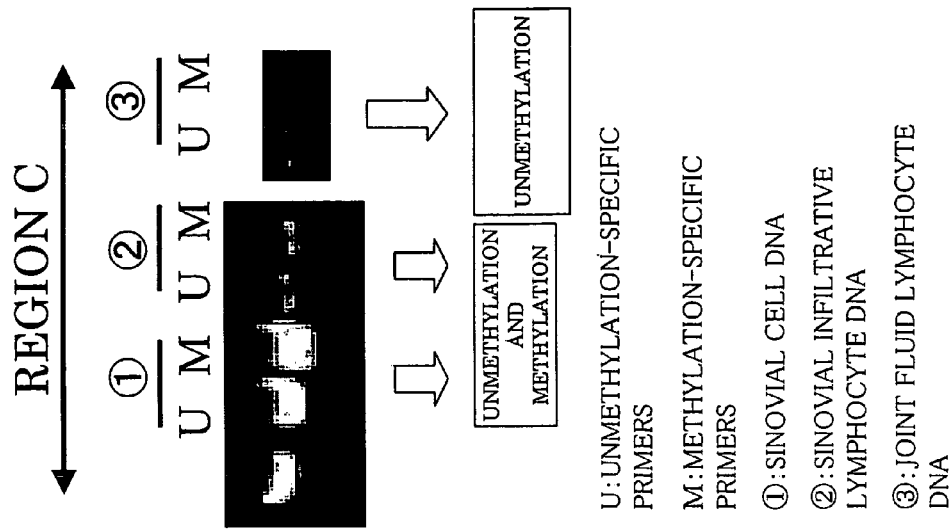

REGION C

① ② ③
U M U M U M

⇒ UNMETHYLATION AND METHYLATION
⇒ UNMETHYLATION

U: UNMETHYLATION-SPECIFIC PRIMERS
M: METHYLATION-SPECIFIC PRIMERS
①: SINOVIAL CELL DNA
②: SINOVIAL INFILTRATIVE LYMPHOCYTE DNA
③: JOINT FLUID LYMPHOCYTE DNA

FIG. 6

|  | | REGION A | | | REGION B | | | REGION C | | |
|---|---|---|---|---|---|---|---|---|---|---|
|  | N | U | U/M | M | U | U/M | M | U | U/M | M |
| PBMC | | | | | | | | | | |
|   Healthy | 9 | 0 | 0 | 9 | 0 | 9 | 0 | 9 | 0 | 0 |
|   RA | 10 | 0 | 0 | 10 | 0 | 10 | 0 | 10 | 0 | 0 |
| SAC | | | | | | | | | | |
|   OA | 15 | 0 | 4 | 11 | 0 | 15 | 0 | 6 | 8 | 1 |
|   RA | 24 | 0 | 0 | 24 | 0 | 22 | 2 | 0 | 15 | 9 |

N: THE NUMBER OF SAMPLES  PBMC: PERIPHERAL BLOOD LYMPHOCYTES

SAC: SINOVIAL CELLS

U: UNMETHYLATION

U/M: UNMETHYLATION AND METHYLATION

M: METHYLATION

RA LYMPHOCYTES (×1000)

RA SINOVIAL CELLS (×1000)

SEQUENCE LISTING

<160> NUMBER OF SEQ ID NOS: 13

<210> SEQ ID NO 1
<211> LENGTH: 592
<212> TYPE: DNA
<213> ORGANISM: Homo sapiens

<400> SEQUENCE: 1

```
acgccgggct agttttttgta ttttaagtag agacggcatt tcaccatatt ggtcaggctg    60
gtctcgaact cctgacccca agtgttccgc ccgcctctgc ctcccatagt gctagaatta   120
caggcctgag ctactgcgct tggccccttg cggtactttt ggcccaacct cctccatggc   180
tggggacgcg gaggccgaga gagaagtcac ttgccctggc tctaccttga agtggttctc   240
agggttgggg cgagagtcgg ggtggggacc gagatgcagc tctatcctgt gcccctggtc   300
gcagcaggca gcccagcgct tcgcgtgttc tacttggcct gtccgctgcc gcctaatgag   360
ctcaggtcta ggccgagcag aggggcacc tggtcggact cggttgggct cgggcggccc    420
cgcctccccc cgcccgccag gcgggcccctt ctcgacggcg cggggcgggc cctgcgggcg   480
cggggctgaa ggcggaacca cgacgggcag agagcacgga gccgggaagc ccctgggcgc   540
ccgtcggagg gctatggagc agcggccgcg gggctgcgcg gcggtggcgg cg            592
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 2

```
gttttatttg gtttgttcgt tgtc                                            24
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 3

```
cgtactctct acccgtcgta a                                               21
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 4

```
tttatttggt ttgtttgttg ttgtt                                           25
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 5
actccatact ctctacccat cataa                                          25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 6
ttgattttaa gtgtttcgtt cgtt                                           24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 7
aaacgctaaa ctacctacta cgacc                                          25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 8
gattttaagt gttttgtttg tt                                             22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 9
aacactaaac tacctactac aacc                                           24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 10
gtagtaggta gtttagcgtt tcgc                                           24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Polynucleotide -continued

```
<400> SEQUENCE: 11 caaataccccc ctctactcga c                                                21

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 12
tagtaggtag tttagtgttt tgtgt                                             25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      Artificially Synthesized Polynucleotide

<400> SEQUENCE: 13
accaaatacc ccctctactc aac                                               23
```

METHODS FOR DIAGNOSING RHEUMATOID ARTHRITIS

This application is the US national phase of international application PCT/JP2004/017497, filed 25 Nov. 2004, which designated the U.S. and claims priority of JP 2004-052495, filed 26 Feb. 2004; JP 2004-112548, filed 6 Apr. 2004; JP 2004-247525, filed 26 Aug. 2004; and JP 2004-297965, filed 12 Oct. 2004, the entire contents of each of which are hereby incorporated by reference.

TECHNICAL FIELD

The present invention relates to a polynucleotide associated with development of rheumatoid arthritis, and a method and kit for determining development of rheumatoid arthritis or the likelihood of developing rheumatoid arthritis. The invention also relates to a medicament for treating rheumatoid arthritis, using the polynucleotide.

BACKGROUND ART

Rheumatoid arthritis (hereinafter referred to as "RA") is a systemic inflammatory disorder of unknown etiology, often characterized by frequent occurrence of erosive arthritis and also involving disorders in multiple organs. RA chronically progresses by repeating a cycle of remission and exacerbation, and, if untreated, causes destruction or deformation of joints, which eventually leads to functional disabilities in motor organs and sometimes death. Therefore, RA causes huge physical and psychological pain throughout the life of a patient.

RA develops in a variety of ways, and the guidelines proposed by the American College of Rheumatology are widely used for the diagnosis. However, RA usually develops gradually over the course of several weeks to several months, and the percent positive for the rheumatoid factor, which is used as an objective measure of RA diagnosis according to the foregoing guidelines, is only about 33% within 3 months and does not go beyond 88% even within 12 months or longer (see Non-Patent Document 1: Treatment, Vol. 73, No. 3, pp. 23-27, 1991). That is, there is inaccuracy in RA diagnosis. In view of this, there have been attempts to diagnosis RA by detecting RA-associated anti-IgM antibody that reacts with a recombinant antigen in the serum of a patient (see Patent Document 1: Japanese Laid-Open Patent Publication No. 10-513257 (published on Dec. 15, 1998)).

Further, the treatment of RA generally follows different paths depending upon the progress of the pathology. In the early stage of RA where the diagnosis is generally premature, the treatment involves administration of non-steroidal anti-inflammatory drugs (NSAID). This is followed by additional administration of disease-modifying antirheumatic drugs (DMARD), once the diagnosis becomes definitive. Specifically, in the initial stage of RA development where definitive diagnosis cannot be made easily, the treatment begins with the administration of NSAID, and while carefully monitoring the progress, an evaluation is made to distinguish whether the patient is actually suffering from RA or other rheumatoid disorders including collagenosis. If the symptoms progress, steroid drugs may be administered, and the drug therapy for relieving pain is performed in combination with physical therapy and device therapy, which are intended to maintain and restore the joint functions. Surgery may be performed if daily living activities were disabled by damaged joints.

As described in Patent Document 2 (International Publication WO98/51791 (published on Nov. 19, 1998)), the inventors of the present invention have performed linkage analysis on RA patients and their kin group using micro satellite markers, and specified 3 loci for RA genes. Specifically, the following affected genes have been identified.

(1) RA gene located on human chromosome 1 within ±1 centiMorgan of the DNA sequence that hybridizes with micro satellite marker D1S214 and/or D1S253

(2) RA gene located on human chromosome 8 within ±1 centiMorgan of the DNA sequence that hybridizes with micro satellite marker D8S556

(3) RA gene located on human X chromosome within ±1 centiMorgan of the DNA sequence that hybridizes with micro satellite marker DXS1001, DXS1047, DXS1205, DXS1227, and/or DXS1232

Further, as described in Non-Patent Document 2 (Rheumatism, Vol. 39, No. 2, pp. 444-445, 1999), the inventors of the present invention, from the RA-associated genes of the prior invention, has identified death receptor 3 ("DR3" or "DR3 gene") as a candidate for the RA-associated gene for markers D1S214 and D1S253 as set out in (1) above. Concerning DR3, the inventors have confirmed restriction fragment length polymorphism between healthy subjects and RA patients, and suggested the possibility that DR3 might be a gene associated with RA.

In Patent Document 3 (International Publication WO02/34912 (published on May 2, 2002)), the inventors of the present invention have suggested that genomic mutation in DR3 gene might be related to onset of RA (chronic RA).

In higher eukaryotes, methylation is known to occur in portions of genomic DNA sequence with 5'-CG-3' (hereinafter, "CpG" or "CpG sequence"), whereby the cytosine (C) on the 5' end side of guanosine (G) is methylated. The methylation in CpG is believed to have influence on the gene expression, particularly when CpG-rich regions exist within the promoter region of the gene.

As a rule, many genes on the chromosomes are protected from methylation. However, gene transcription is suppressed if, for some reason, methylation occurs in CpG-rich regions in the promoter region. From this, it can be speculated that the effect of CpG methylation on gene expression can impede proper gene activity and cause disease.

However, the methylation state of CpG needs to be studied further for DR3, a possible candidate for RA-associated gene.

DISCLOSURE OF INVENTION

An object of the present invention is to analyze the methylation state of CpG sequences in the promoter region of DR3, and provide a polynucleotide that is useful for revealing the onset mechanism of human rheumatoid arthritis. Another object of the invention is to provide a kit and method for accurately determining development of human RA or the likelihood of developing human RA. The invention also provides a medicament that is effective for the treatment of RA patients with abnormal DR3 gene activity.

In order to achieve the foregoing objects, the inventors of the present invention analyzed the human genome in regard to the DNA methylation in the upstream region (including the promoter region) of the translation initiation point of DR3 gene associated with RA. It was found as a result that allele-specific methylation occurs in CpG sequences located about −380 to −180 bp upstream from the translation initiation point of DR3 gene (ATG). It was further found that the CpG sequences downstream from such translation initiation point of DR3 genes originating in the peripheral blood lymphocytes of healthy subjects and RA patients were all unmethylated, while methylated and unmethylated sequences were both observed in DR3 gene originating in the synovial cells and synovial infiltrating lymphocytes of RA patients.

Further, sequencing of the upstream region of the translation initiation point revealed that a TCCTCC motif exists in the vicinity of −380 bp, and that the allele-specific methylation in the CpG sequences begins in the vicinity of the TCCTCC motif. The present invention was accomplished based on these findings.

Specifically, a polynucleotide according to the present invention comprises the base sequence of SEQ ID NO: 1 and includes a promoter region of DR3 gene associated with RA, wherein the base sequence from base 170 to 175 of the polynucleotide constitutes a TCCTCC motif that is associated with transcription activity, and wherein allele-specific methylation occurs in some of CpG sequences that occur subsequent to the TCCTCC motif.

As used herein, "allele-specific methylation" is intended to mean that methylation occurs specific to the CpG sequences in one of the alleles.

In a polynucleotide according to the present invention, CpG sequences located downstream to −180 bp relative to a translation initiation point of the DR3 gene (base 374 and the subsequent bases in the base sequence of SEQ ID NO: 1) are either methylated or unmethylated. An example of such a polynucleotide is the promoter region of DR3 gene originating in the synovial cells of RA patients.

Further, in a polynucleotide according to the present invention, the allele-specific methylation occurs in CpG sequences located from −380 bp to −180 bp relative to a translation initiation point of the DR3 gene (from base 174 to 373 in the base sequence of SEQ ID NO: 1), and wherein CpG sequences downstream to −180 bp (base 374 and the subsequent bases in the base sequence of SEQ ID NO: 1) are either methylated or unmethylated. An example of such a polynucleotide is the promoter region of DR3 gene originating in the peripheral blood lymphocytes of healthy subjects, or the promoter region of DR3 gene originating in the peripheral blood lymphocytes and synovial infiltrating lymphocytes of RA patients.

A determining kit according to the present invention is for determining development of RA or the likelihood of developing RA, wherein a comparison is made in regard to methylation state between a DR3 promoter region obtained from synovial cells or synovial infiltrating lymphocytes and a DR3 promoter region obtained from peripheral blood lymphocytes, and a characteristic of the kit is to include methylation-specific primers and unmethylation-specific primers, which are used to determine the presence or absence of methylated cytosines in at least a part of a polynucleotide constituting the DR3 promoter region.

As used herein, the "likelihood of developing RA" is a potential risk of developing RA. The greater the likelihood, the greater the risk of developing RA, and the smaller the likelihood, the smaller the risk of developing RA.

In a determining kit according to the present invention, it is preferable that the methylation-specific primers and the unmethylation-specific primers be designed to amplify at least the base sequence from base 374 to 564 of the base sequence set forth in SEQ ID NO: 1. Base 336 to 564 of the base sequence in SEQ ID NO: 1 are promoter region for DR3 gene, and base 374 to 592 of the base sequence in SEQ ID NO: 1 are C region mentioned below.

With a determining kit according to the present invention, it is possible to determine that the subject has developed RA or has the likelihood of developing RA, when the DR3 promoter region obtained from the synovial cells or synovial infiltrating lymphocytes is more strongly methylated than the DR3 promoter region obtained from the peripheral blood lymphocytes, or when the DR3 promoter region obtained from the synovial cells or synovial infiltrating lymphocytes is strongly methylated.

In a determining kit according to the present invention, a DR3 gene originating in the peripheral blood lymphocytes of healthy subjects is used as a control, and the kit determines that the subject has developed RA or has the likelihood of developing RA when the DR3 promoter region obtained from the synovial cells or synovial infiltrating lymphocytes is more strongly methylated than the DR3 promoter region originating in the peripheral blood lymphocytes.

According to the present invention, there is provided a method for determining development of RA or the likelihood of developing RA, the method including: comparing a methylation state of a DR3 promoter region obtained from synovial cells or synovial infiltrating lymphocytes with a methylation state of a DR3 promoter region obtained from peripheral blood lymphocytes, or confirming that the DR3 promoter region obtained from the synovial cells or synovial infiltrating lymphocytes is strongly methylated.

A method according to the present invention may further include: a DNA converting step to convert unmethylated cytosines into uracils in CpG sequences contained in the DR3 promoter region obtained from the synovial cells or synovial infiltrating lymphocytes, and the DR3 promoter region obtained from the peripheral blood lymphocytes, by treating the respective DR3 promoter regions with a bisulfite-containing reagent; a DNA amplifying step to amplify the DR3 promoter regions, after the treatment in the DNA converting step, by a polymerase chain reaction using methylation-specific primers or unmethylation-specific primers; a methylation-state detecting step to detect a methylation state of the DR3 promoter regions by detecting whether the polymerase chain reaction in the DNA amplifying step using the methylation-specific primers or the unmethylation-specific primers has amplified the DR3 promoter regions; and a comparing step to compare the DR3 promoter region obtained from the synovial cells or synovial infiltrating lymphocytes with the DR3 promoter region obtained from the peripheral blood lymphocytes, in regard to the methylation state of the DR3 promoter A regions detected in the methylation-state detecting step, or a confirming step to confirm that the DR3 promoter region obtained from the synovial cells or synovial infiltrating lymphocytes is strongly methylated.

An example of the promoter region of DR3 gene is a polynucleotide with the base sequence from base 336 to 564 in the base sequence of SEQ ID NO: 1.

With a method according to the present invention, it is possible to determine that the subject has developed RA or has the likelihood of developing RA, when the DR3 promoter region obtained from the synovial cells or synovial infiltrating lymphocytes is more strongly methylated than the DR3 promoter region obtained from the peripheral blood lymphocytes. This method provides highly accurate diagnosis of RA development or the likelihood of developing RA in human.

A method according to the present invention may be adapted so that a DR3 gene originating in the peripheral blood lymphocytes of healthy subjects is used as a control, and that the method determines that the subject has developed RA or has the likelihood of developing RA when the DR3 promoter region obtained from the synovial cells or synovial infiltrating lymphocytes is more strongly methylated than the DR3 promoter region originating in the peripheral blood lymphocytes.

A medicament for treating RA according to the present invention includes a DR3 gene whose promoter region is part of a polynucleotide wherein CpG sequences located from −380 bp to −180 bp relative to the translation initiation point of DR3 gene are either methylated or unmethylated, and CpG sequences downstream to −180 bp are unmethylated.

Preferably, the medicament is administered to the synovial cells or synovial infiltrating lymphocytes of RA patients.

As used herein, "A", "C", "G", and "T" denote adenine, cytosine, guanine, and thymine, respectively, unless otherwise noted.

Additional objects, features, and strengths of the present invention will be made clear by the description below. Further, the advantages of the present invention will be evident from the following explanation in reference to the drawings.

BRIEF DESCRIPTION OF DRAWINGS

FIG. 5(a) is a diagram showing results of polyacrylamide gel electrophoresis, performed according to the MSP method described in Example, on DNA fragments that were obtained in A region in the upstream region of DR3 gene and amplified in a DNA amplifying step, wherein the numbers 1 to 3 in circles indicate gene originating in the synovial cells, gene originating in the synovial cell fluid lymphocytes, and gene originating in joint fluid lymphocytes, respectively.

FIG. 5(b) is a diagram showing results of polyacrylamide gel electrophoresis, performed according to the MSP method described in Example, on DNA fragments that were obtained in B region in the upstream region of DR3 gene and amplified in a DNA amplifying step, wherein the numbers 1 to 3 in circles indicate gene originating in the synovial cells, gene originating in the synovial cell fluid lymphocytes, and gene originating in joint fluid lymphocytes, respectively.

FIG. 5(c) is a diagram showing results of polyacrylamide gel electrophoresis, performed according to the MSP method described in Example, on DNA fragments that were obtained in C region in the upstream region of DR3 gene and amplified in a DNA amplifying step, wherein the numbers 1 to 3 in circles indicate gene originating in the synovial cells, gene originating in the synovial cell fluid lymphocytes, and gene originating in joint fluid lymphocytes, respectively.

FIG. 6 is a table showing results of investigation performed according to the MSP method described in Example and in regard to the methylation state in the upstream region of DR3 gene originating in the peripheral blood lymphocytes (PBMC) of healthy subjects and RA patients, and the synovial cells (SAC) of RA patients and OA patients.

BEST MODE FOR CARRYING OUT THE INVENTION

The following will describe the present invention in detail. It should be appreciated that the present invention is not limited in any way by the following description.

[1] Polynucleotide of the Present Invention

A polynucleotide according to the present invention comprises the base sequence of SEQ ID NO: 1 and includes a promoter region of a rheumatoid arthritis-associated gene DR3. In the polynucleotide, the base sequence from base 170 to 175 comprises a TCCTCC motif associated with transcription activity, and some of the CpG sequences subsequent to the TCCTCC motif are modified by allele-specific methylation.

The base sequence of SEQ ID NO: 1 covers a region upstream of the translation initiation point of DR3, which is one of the rheumatoid arthritis-associated genes originating in human genome as described in Non-Patent Document 2, and +39 bp downstream of the translation initiation point (covering from −553 bp upstream to −1 bp downstream of the translation initiation point, by taking the adenine of the translation initiation point (ATG) as a reference at +1 bp (hereinafter, may be referred to as "upstream region of DR3")). By a study conducted by the inventors of the present invention, the sequence "TCCTCC" covering from −379 bp to −384 bp in the upstream region of DR3 (base 170 to 175 of SEQ ID NO: 1) was found to constitute a TCCTCC motif associated with the transcription activity of DR3 gene. It was also found that some of the CpG sequences subsequent to the TCCTCC motif were modified by allele-specific methylation.

As used herein, "subsequent to the TCCTCC motif" is intended to mean a region downstream (toward the 3' end) of a TCCTCC motif portion of a polynucleotide of the present invention.

Figure 1:
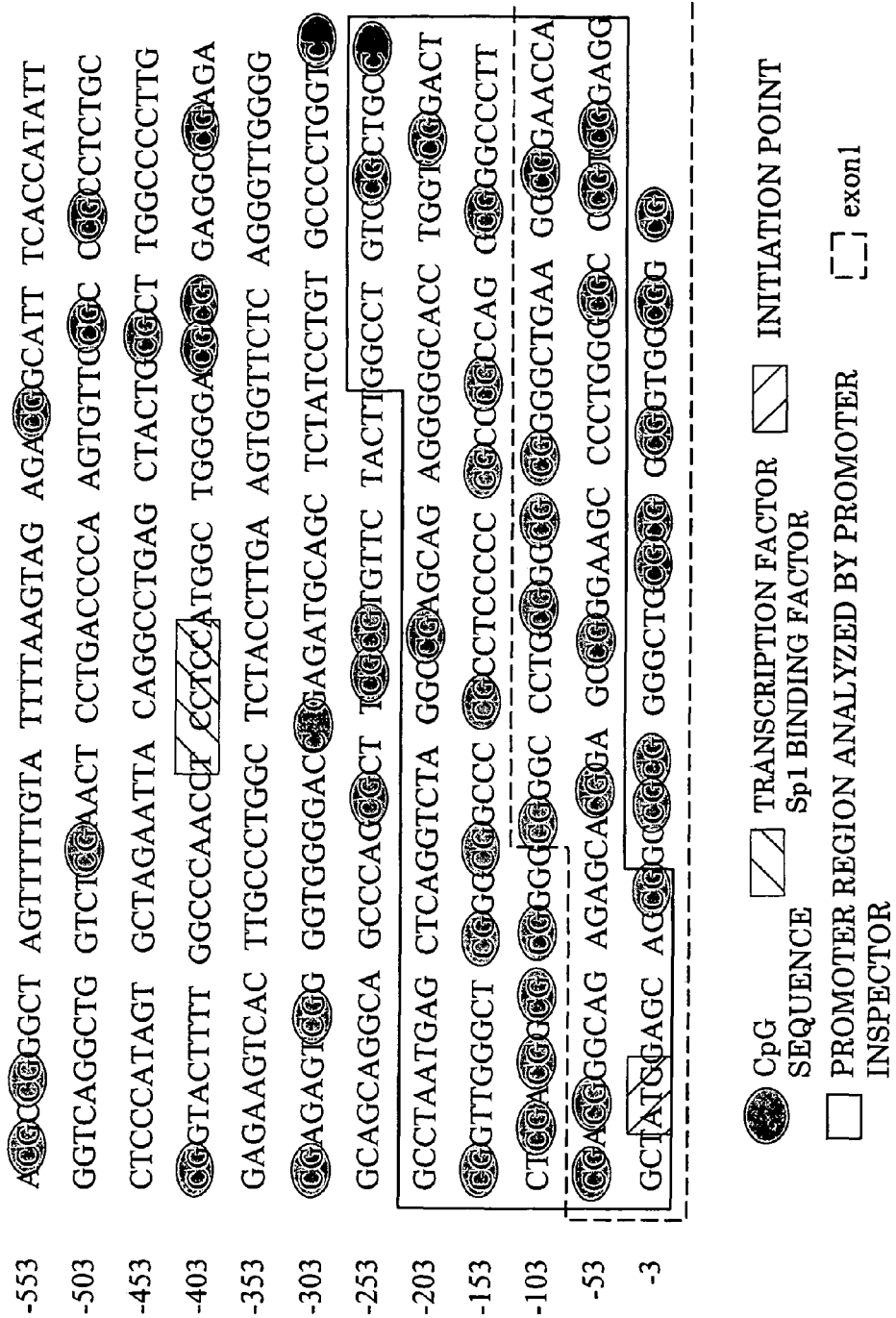
FIG. 1 is a diagram showing a base sequence of a polynucleotide according to the present invention.

FIG. 1 represents a base sequence of a polynucleotide according to the present invention. The base sequence shown in FIG. 1 includes part of the base sequence subsequent to the DR3 gene translation initiation point constituting exon 1 of DR3 gene. FIG. 1 also illustrates CpG sequences, the TCCTCC motif (shown as "transcription factor Sp1 binding factor"), the translation initiation point, a promoter region, and exon 1.

As shown in FIG. 1, a polynucleotide according to the present invention includes a multiplicity of CpG sequences. Some of the CpG sequences are methylated. In the polynucleotide sequence set forth in SEQ ID NO: 1, a region from base 1 to 173 is designated as A region, a region from base 174 to 373 B region, and a region from base 374 to 592 C region. In the base sequence shown in FIG. 1, the area surrounded by solid lines (corresponding to base 336 to 564 in the base sequence of SEQ ID NO: 1) is a region identified as a promoter in the analysis performed with a promoter inspector. The promoter partially overlaps the C region. The area surrounded by broken lines is exon 1.

Figure 2:
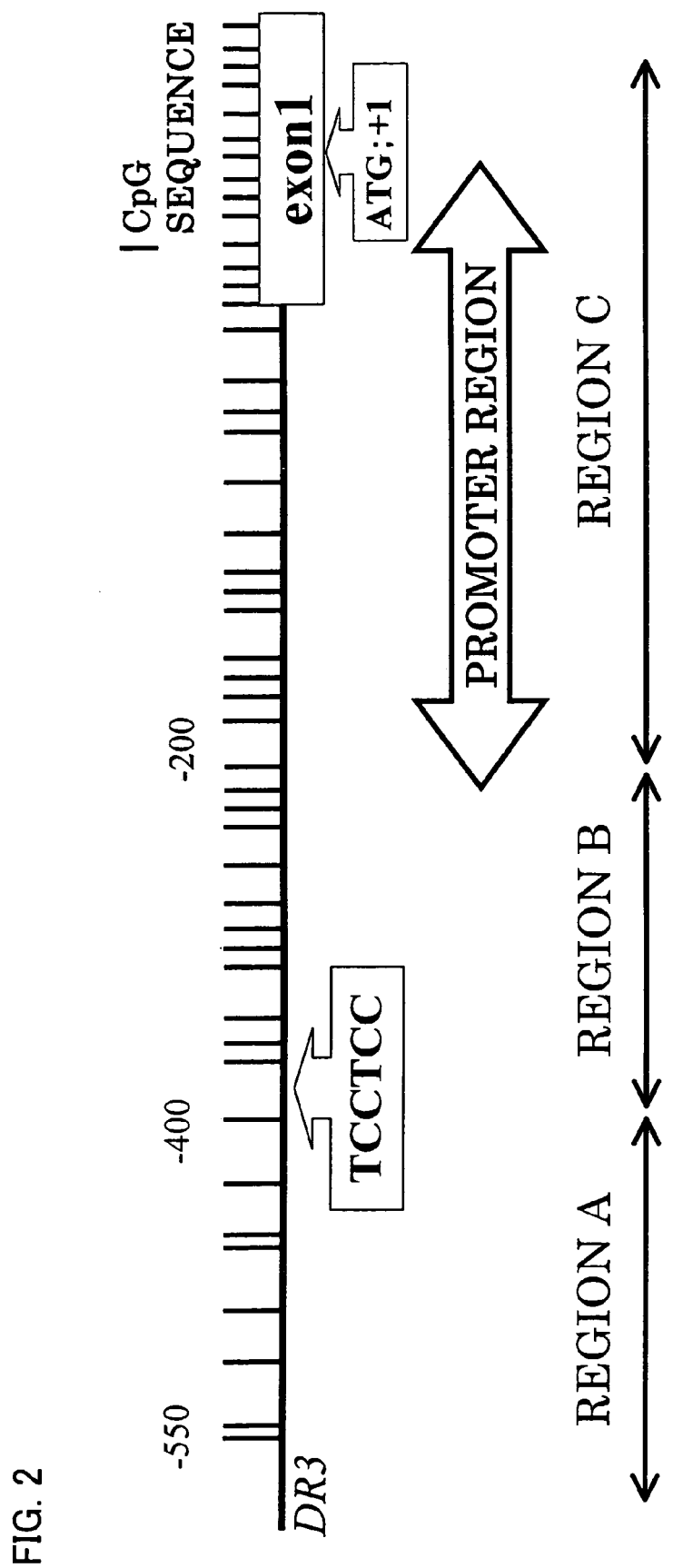
FIG. 2 is a diagram schematically illustrating a structure of the polynucleotide comprised of the base sequence of FIG. 1.

FIG. 2 shows a structure of the polynucleotide having the base sequence of FIG. 1. More specifically, FIG. 2 schematically illustrates a structure of a region located upstream of the translation initiation point of DR3 gene. Among the polynucleotide elements shown in FIG. 2 are CpG sequences, TCCTCC motif, exon 1, translation initiation point (ATG), and A, B, and C regions. As shown in FIG. 2, the promoter region of DR3 gene substantially coincides with C region.

The polynucleotide shown in FIGS. 1 and 2, i.e., the polynucleotide having the base sequence of SEQ ID NO: 1 includes CpG sequences at base 2, 3, 5, 6, 34, 35, 65, 66, 88, 89, 92, 93, 137, 138, 151, 152, 187, 188, 189, 190, 196, 197, 251, 252, 258, 259, 270, 271, 300, 301, 317, 318, 322, 323, 324, 325, 344, 345, 350, 351, 374, 375, 395, 396, 401, 402, 411, 412, 415, 416, 421, 422, 431, 432, 435, 436, 442, 443, 453, 454, 456, 457, 459, 460, 461, 462, 466, 467, 475, 476, 479, 480, 481, 482, 493, 494, 501, 502, 504, 505, 517, 518, 523, 524, 538, 539, 542, 543, 545, 546, 563, 564, 567, 568, 569, 570, 577, 578, 579, 580, 582, 583, 588, 589, 591, and 592.

The inventors of the present invention obtained sequences of the upstream region of DR3 gene from DNA extracted from peripheral blood lymphocytes and synovial cells of healthy subjects and RA patients. These sequences were analyzed in regard to the methylation state of CpG sequences in A, B, and C regions.

In A region, the result showed methylation in all of the CpG sequences in both healthy subjects and RA patients. In B region, methylated CpG sequences and unmethylated CpG sequences coexisted both in healthy subjects and RA patients.

In C region, none of the CpG sequences in the upstream region of DR3 gene were methylated in samples obtained from the peripheral blood lymphocytes of healthy subjects and RA patients. In samples obtained from the synovial cells and synovial infiltrating lymphocytes of RA patients, the upstream region of DR3 region in C region contained both methylated and unmethylated CoG sequences as in B region.

In the description of the embodiment, the synovial cells and synovial infiltrating lymphocytes will be collectively referred to as synovial tissues.

It can be said from these results that the base sequence in the upstream region of DR3 gene, obtained from the synovial tissues of RA patients is one specific example of a polynucleotide of the present invention. Such polynucleotide has the base sequence of SEQ ID NO: 1, and includes allele-specifically methylated CpG sequences from −380 bp to −180 bp (B region), and methylated and unmethylated CpG sequences in a region downstream of −180 bp (C region), relative to the translation initiation point of DR3.

The base sequence in the upstream region of DR3 gene, obtained from the peripheral blood lymphocytes of healthy subjects or RA patients is another specific example of a polynucleotide of the present invention. Such polynucleotide has the base sequence of SEQ ID NO: 1, and includes allele-specific methylation in CpG sequences located from −380 bp to −180 bp (B region), and is unmethylated for all of the CpG sequences in a region downstream of −180 bp (C region), relative to the translation initiation point of DR3. The polynucleotide originating in the synovial cells of RA patients has the base sequence of SEQ ID NO: 1, and includes allele-specifically methylated CpG sequences from −380 bp to −180 bp (B region), and methylated and unmethylated CpG sequences in a region downstream of −180 bp (C region), relative to the translation initiation point of DR3.

The foregoing results suggest that a polynucleotide of the present invention has important roles in the expression of DR3 gene. Therefore, a polynucleotide of the present invention can advantageously be used to elucidate the mechanism of RA onset, much of which is unknown. Further, a polynucleotide of the present invention may be useful for the diagnosis of RA, determination of the likelihood of developing the disease, and the treatment of RA.

[2] A Method for Determining Development of RA or the Likelihood of Developing RA According to the Present Invention.

A method for determining development of RA or the likelihood of developing RA according to the present invention is to compare the promoter regions of DR3 gene in regard to the methylation state between samples obtained from the synovial tissues and the peripheral blood lymphocytes.

The promoter region of DR3 gene may be any conventionally known as a promoter region of DR3 gene. One example is a base sequence from base 336 to 564 in the base sequence of SEQ ID NO: 1.

As to the methylation state in the promoter region of DR3 gene, samples obtained from the peripheral blood lymphocytes of healthy subjects had all of the CpG sequences unmethylated, as described above. In RA patients, the promoter region of DR3 gene showed stronger methylation in samples obtained from the synovial tissues than in samples obtained from the peripheral blood lymphocytes.

A method for determining development of RA or the likelihood of developing RA according to the present invention is based on these results. Specifically, the method determines that a subject has developed RA or is likely to develop RA when the promoter region of DR3 gene shows stronger methylation in samples obtained from the synovial tissues than in samples obtained from the peripheral blood lymphocytes.

With regard to the extraction of DNA from the synovial tissues of the subject and obtainment of the promoter region of DR3 gene in the determining method according to the present invention, any conventionally known method of purifying target genes can be used.

In a study conducted by the inventors of the present invention, the inventors have found out that the methylation state in the promoter region of DR3 gene was different between samples obtained from the synovial tissues of RA patients and that obtained from the synovial tissues of healthy subjects. Based on this finding, as a method for determining development of RA or the likelihood of developing RA according to the present invention, it is possible to detect a methylation state in the promoter region of DR3 gene in samples obtained from the synovial tissues, and decide that the subject has not developed RA or has a low likelihood of developing RA when none of the CpG sequences is methylated, and that the subject has developed RA or has a high likelihood of developing RA when the promoter region includes unmethylated and methylated CpG sequences.

This method is slightly less accurate than the method in which the promoter regions of DR3 gene are compared in regard to the methylation state between peripheral blood lymphocytes and synovial tissues. However, since the method does not require obtaining the promoter region of DR3 gene from the peripheral blood lymphocytes, the method simplifies the sample collecting procedure and is therefore able to conveniently determine whether the subject has developed RA or has the likelihood of developing RA.

Conventional methods can be used to detect a methylation state in the CpG sequences of the polynucleotide. Some of the examples include: bisulfite genomic sequencing method (see Clark S J, Harrison J, Paul C L, and Frommer M. High sensitivity mapping of methylated cytosines. Nucleic Acids Res 22, 2990-2997 (1994)), and an MSP method (methylation specific PCR method) (see Harman J G, Graff J R, Myohanen S et al. Methylation-specific PCR: A novel PCR assay for methylation state of CpG islands. Proc Natl Acad Sci 93, 9821-9826 (1996)).

The following Section (3) describes one specific implementation of the method that detects a methylation state of the CpG sequences. In this example, the MSP method was used.

[3] A Kit for Determining Development of RA or the Likelihood of Developing RA.

A determining kit according to the present invention is characterized to compare promoter regions of DR3 gene in regard to the methylation state, wherein the comparison is made between samples obtained from the synovial tissues and samples obtained from the peripheral blood lymphocytes, so as to determine development of RA or the likelihood of developing RA. The determining kit includes methylation-specific primers and unmethylation-specific primers, which are used to determine the presence or absence of methylated cytosines in at least part of the polynucleotide constituting the promoter region of DR3 gene.

As used herein, "at least part of the polynucleotide constituting the promoter region of DR3 gene" is intended to mean at least part of the upstream region of DR3 gene associated with human RA. The polynucleotide may be, for example, part of a polynucleotide having the base sequence of SEQ ID NO: 1, and that includes the promoter region (base 336 to 553 of SEQ ID NO: 1).

Among A, B, and C regions in the upstream region of DR3, the methylation state in C region was found to be different between healthy subjects and RA patients. Specifically, in samples obtained from the peripheral blood lymphocytes and the synovial tissues, C region in the upstream region of DR3 had all of the CpG sequences unmethylated in the peripheral blood lymphocytes of healthy subjects. In RA patients, all of the CpG sequences were unmethylated in C region in samples obtained from the peripheral blood lymphocytes, whereas samples obtained from the synovial tissues had both methylated and unmethylated CpG sequences in C region. That is, the samples from the synovial tissues had a stronger methylation state than samples obtained from the peripheral blood lymphocytes.

A determining kit of the present invention takes advantage of these findings, and determines development of RA or the likelihood of developing RA by comparing samples obtained from the synovial tissues and peripheral blood lymphocytes of subjects, wherein the comparison is made in regard to the methylation state between C region of DR3 gene (or a region including the promoter region) obtained from the synovial tissues and the promoter region of DR3 gene obtained from the peripheral blood lymphocytes.

The determining kit includes methylation-specific primers and unmethylation-specific primers for determining the presence or absence of methylated cytosines. These primers are not particularly limited as long as they can amplify at least part of the promoter region of DR3 gene to determine the presence or absence of methylated cytosines in at least part of the polynucleotide constituting the promoter region.

As used herein, the "unmethylation-specific primers" refers to oligonucleotide primers that are designed to specifically anneal with the DR3 promoter region including CpG sequences. More specifically, the unmethylation-specific primers are primers in which all the cytosines (C) in the promoter region have been converted to thymines (T).

As used herein, the "methylation-specific primers" refers to oligonucleotide primers that are designed to specifically anneal with the DR3 promoter region including CpG sequences. More specifically, the methylation-specific primers are oligonucleotide primers in which all the cytosines (C) in the promoter region have been converted to thymines (T) except in the CpG sequences.

By being designed this way, the methylation-specific primers can specifically anneal (complement) with the promoter region containing the methylated CpG sequences. Preferably, the forward primers and reverse primers are both designed to specifically anneal with the promoter region containing the methylated CpG sequences.

One specific example of the unmethylation-specific primers are oligonucleotide primers that are designed for CpG sequence regions that exist in the promoter region of DR3 gene, and in which all the cytosines (C) in the promoter region have been converted to thymines (T).

One specific example of the methylation-specific primers are oligonucleotide primers that are designed for CpG sequence regions that exist in the promoter region of DR3 gene, and in which all the cytosines (C) in the promoter region have been converted to thymines (T) except in the CpG sequences.

More specifically, the methylation-specific primers and the unmethylation-specific primers may be designed so that the region with the methylated CpG sequences and the region without the methylated CpG sequences from base 374 to 564 of the base sequence set forth in SEQ ID NO: 1 can be respectively amplified by these primers. Specific examples of the methylation-specific primers are:

```
Forward primer (MF3):
GTTTTATTTG GTTTGTTCGT TGTC      (SEQ ID NO: 2)

Reverse primer (MR3):
CGTACTCTCT ACCCGTCGTA A.        (SEQ ID NO: 3)
```

A specific example of the unmethylation-specific primers is:

```
Forward primer (UF3):
TTTATTTGGT TTGTTTGTTG TTGTT     (SEQ ID NO: 4)

Reverse primer (UR3):
ACTCCATACT CTCTACCCAT CATAA.    (SEQ ID NO: 5)
```

The following describes the procedures by which a determining kit of the present invention is used to perform the method for determining development of RA or the likelihood of developing RA.

(1) DNA Converting Step

The DR3 promoter region obtained from subjects according to known methods is first subjected to the DNA converting step. In this step, only the unmethylated cytosines in the CpG sequences of the promoter region are converted to uracils.

In the DNA converting step, the DR3 promoter region is treated with a bisulfite-containing reagent to convert unmethylated cytosines to uracils in the CpG sequences of the promoter region. Specific methods or conditions are not particularly limited.

In the DNA converting step, unmethylated cytosines in the CpG sequences are converted to uracils by the bisulfite treatment. Since the bisulfite treatment has no effect on methylated cytosines, the presence or absence of methylated cytosines in the CpG sequences can be determined based on whether the bisulfite treatment has converted cytosines to uracils. That is, even with the DNA of the same base sequence, the presence or absence of methylation causes changes in the base sequence by the bisulfite treatment.

Alternatively, the base sequences after the bisulfite treatment may be sequences and the presence or absence of methylation in the CpG sequences can be detected based on differences in the base sequences. This is known as a bisulfite genome sequencing method.

The "bisulfite-containing reagent" is not particularly limited as long as it contains conventionally known bisulfite. A preferable example is sodium bisulfite ($NaHSO_3$). Further, a bisulfite compound and urea may be used together.

The DR3 gene promoter region used for the detection of methylation is obtained from the genomic DNA extracted from the human synovial tissues or human peripheral blood lymphocytes.

(2) DNA Amplifying Step.

The DNA fragments of the promoter region subjected to the bisulfite treatment in the DNA converting step are amplified by the DNA amplifying step.

In the DNA amplifying step, the DNA fragments obtained in the DNA converting step are amplified by polymerase chain reaction (PCR). The methylation-specific primers are used for the DNA fragments in which unmethylated cytosines have been converted to uracils, and the unmethylation-specific primers are used for the DNA fragments that have retained methylated cytosines without conversion. Specific methods and conditions are not particularly limited.

In the DNA amplifying step, whether cytosines in the CpG sequences have been converted to uracils is determined by PCR using the methylation-specific primers of the determining kit. The methylation-specific primers specifically anneal (complement) with the CpG-containing DNA fragments (hereinafter "methylated CpG-containing DNA) that have retained the cytosines in the CpG sequences without conversion by the bisulfite treatment. Thus, PCR using the methylation-specific primers specifically amplifies DNA fragments that include methylated CpG sequences. As the methylation-specific primers, the foregoing MF3 and MR3 may be used.

The CpG-containing DNA fragments (hereinafter "unmethylated CpG-containing DNA") that have converted cytosines in the CpG sequences to uracils by the bisulfite treatment do not anneal with the methylation-specific primers, and are not amplified by the methylation-specific primers.

For this reason, the DNA amplifying step includes another amplifying step in which the CpG-containing DNA that has converted methylated cytosines to uracils in the DNA converting step is amplified by PCR using the unmethylation-specific primers.

PCR using the unmethylation-specific primers amplifies unmethylated CpG-containing DNA but do not amplify methylated CpG-containing DNA. As the unmethylation-specific primers, the foregoing UF3 and UR3 may be used.

By checking whether the PCR using the methylation-specific primers and unmethylation-specific primers has amplified DNA samples, the presence or absence of methylated cytosines in the CpG sequences can be detected.

In the case where a single DNA fragment includes methylated cytosines and unmethylated cytosines, the DNA fragment is amplified by both PCR using the methylation-specific primers and PCR using the unmethylation-specific primers.

As used herein, "polymerase chain reaction" means PCR commonly known in the art. Specific methods and conditions are not particularly limited.

(3) Methylation Detecting Step

A method for determining development of RA or the likelihood of developing RA according to the present invention further includes a methylation-detecting step. The methylation-detecting step detects whether the DNA amplifying step has amplified the CpG-containing DNA fragments (i.e., DR3 promoter region). Specific methods and conditions are not particularly limited.

PCR using the methylation-specific oligonucleotide primers is used to detect whether the CpG-containing DNA fragments have been amplified. In this way, the presence or absence of methylated cytosines in the base sequence of the CpG-containing DNA can be detected both conveniently and quickly, with good sensitivity.

Specifically, detection can be made, for example, by labeling the primers with fluorescent labels, biotin labels, DIG labels, or radioisotope labels, or by performing gel electrophoresis, real time PCR, capillary electrophoresis, fragment analysis, or immunostaining. Any device and method can be used for the detection.

(4) Comparing Step

A method for determining development of RA or the likelihood of developing RA according to the present invention further includes a comparing step. The comparing step compares the DR3 gene promoter regions between samples obtained from the synovial tissues and samples obtained from the peripheral blood lymphocytes, wherein the comparison is made in regard to the methylation state as detected in the methylation detecting step. Based on the result of comparison, determination is made as to development of RA or the likelihood of developing RA.

For example, a subject is deemed to have developed RA or have the likelihood of developing RA when the comparing step finds that the DR3 gene promoter region collected from the synovial tissues is more strongly methylated than the DR3 gene promoter region collected from the peripheral blood lymphocytes.

In place of the comparing step, the determining method of the present invention may include a confirming step of confirming that the DR3 gene promoter region collected from the synovial tissues is strongly methylated. In the confirming step, the state of methylation in the DR3 gene promoter region collected from the synovial tissues can be detected by the method used for this purpose in the methylation-detecting step. A subject can be deemed to have developed RA or have the likelihood of developing RA when the detection of methylation state finds that the DR3 promoter region collected from the synovial tissues is strongly methylated. As used herein, "strongly methylated" refers to the state in which 70% or greater than 70% of the CpG sequences in the polynucleotide are methylated.

In this way, the DR3 gene promoter regions obtained from subjects can be used to determine whether the subjects have developed RA or have the likelihood of developing RA.

A determining kit of the present invention is not particularly limited as long as it includes at least the methylation-specific primers and the unmethylation-specific primers. However, for improved convenience, the determining kit preferably includes a bisulfite reagent for converting unmethylated cytosines to uracils in the CpG sequences of the subject's promoter region.

More preferably, the kit also includes PCR reagents, which can be selected from conventionally available reagents used for PCR.

As described above, a determining kit according to the present invention can be used to conveniently and easily perform the method for determining development of RA or the likelihood of developing RA.

As will be described later in Example, DR3 gene has been shown to be specifically expressed in the synovial tissues (synovial cells, synovial infiltrating lymphocytes) of RA patients. It is therefore conceivable that the difference in the methylation state of the DR3 gene promoter region is associated with the expression of DR3 gene in the synovial tissues and therefore the development of RA. That is, it can be said from the foregoing results that the determining kit and determining method of the present invention are indeed effective for the determination of RA development or the likelihood of RA development.

[4] RA Medicament of the Present Invention

A RA medicament according to the present invention includes DR3 gene that has a promoter region, with unmethylated CpG sequences, in a polynucleotide of the present invention. More specifically, A medicament according to the present invention includes DR3 gene that has a promoter region in part of the base sequence of SEQ ID NO: 1, wherein the promoter region includes allele-specific methylation in CpG sequences located from −380 bp to −180 bp, and is unmethylated for all of the CpG sequences in a region downstream of −180 bp, relative to the translation initiation point of DR3.

The medicament is particularly suited for RA patients whose DR3 gene has a strongly methylated promoter region.

As will be described later in Example, RA patients and healthy subjects have the same methylation state in the DR3 promoter region originating in the peripheral blood lymphocytes; however, the methylation state is different between RA patients and healthy subjects in samples originating in the synovial tissues. This suggests that, in order for DR3 gene to function properly, it may be necessary for the DR3 gene promoter region in the synovial tissues to be methylated. A medicament of the present invention is therefore preferably administered to the synovial tissues of RA patients.

The following will describe the present invention in more detail by way of Example. It should be appreciated that the present invention is not limited in any way by the following description, but may be altered in a variety of ways. Further, the present invention is not limited to the description of the embodiments above, but may be altered by a person ordinary skill in the art within the scope of the claims. An embodiment based on a proper combination of technical means disclosed in different embodiments is encompassed in the technical scope of the present invention.

Example

The MSP method was used to detect a methylation state in the upstream region of the translation initiation point of DR3 gene contained in the DNA obtained from the human peripheral blood lymphocytes, human synovial cells, and human synovial infiltrating lymphocytes. The following describes the methods and the results.

(1) Detection of Methylation State by MSP Method

First, the peripheral blood lymphocytes and synovial cells were collected from healthy subjects and RA patients according to conventional methods. After bisulfite treatment, detection was made on methylation state of the CpG sequences contained in the base sequence in the upstream region of DR gene in each sample, using the MSP method described in the foregoing embodiment.

Specific procedures and reagents used for the bisulfite treatment are as follows:

(1) Add NaOH (denature DNA into a single strand)
(2) Allow the sample to stand for 30 minutes at 37° C.
(3) Add sodium bisulfite ($NaHSO_3$)/hydroquinone ($C_6H_6O_2$) (pH 5.0) to initiate sulfonation and deamination
(4) Leave the sample in dark for 20 hours at 55° C.
(5) Desalination with Wizard DNA Clean-up System (desulfonation)
(6) Add NaOH (alkali treatment)
(7) Allow the sample to stand for 10 minutes at 37° C.
(8) Add ammonium acetate/EtOH, invert to mix, and precipitate with ethanol
(9) Dissolve in distilled water (completion of bisulfite DNA).

For the amplification of A, B, and C regions, the following methylation-specific primers and unmethylation-specific primers were used.

```
Methylation-specific primers for A region:
Forward primer (MF1):
TTGATTTTAA GTGTTTCGTT CGTT      (SEQ ID NO: 6)

Reverse primer (MR1):
AAACGCTAAA CTACCTACTA CGACC     (SEQ ID NO: 7)

Unmethylation-specific primer for A region:
Forward primer (UF1):
GATTTTAAGT GTTTTGTTTG TT        (SEQ ID NO: 8)
```

-continued

```
Reverse primer (UR1):
AACACTAAAC TACCTACTAC AACC      (SEQ ID NO: 9)

Methylation-specific primer for B region:
Forward primer (MF2):
GTAGTAGGTA GTTTAGCGTT TCGC      (SEQ ID NO: 10)

Reverse primer (MR2):
CAAATACCCC CTCTACTCGA C         (SEQ ID NO: 11)

Unmethylation-specific primer for B region:
Forward primer (UF2):
TAGTAGGTAG TTTAGTGTTT TGTGT     (SEQ ID NO: 12)

Reverse primer (UR2):
ACCAAATACC CCCTCTACTC AAC       (SEQ ID NO: 13)

Methylation-specific primer for C region:
Forward primer (MF3):
GTTTTATTTG GTTTGTTCGT TGTC      (SEQ ID NO: 2)

Reverse primer (MR3):
CGTACTCTCT ACCCGTCGTA A         (SEQ ID NO: 3)

Unmethylation-specific primer for C region:
Forward primer (UF3):
TTTATTTGGT TTGTTTGTTG TTGTT     (SEQ ID NO: 4)

Reverse primer (UR3):
ACTCCATACT CTCTACCCAT CATAA     (SEQ ID NO: 5)
```

PCR was performed with the following cycling parameters: one cycle consisting of 10 minutes at 95° C.; cycles consisting of 1 minute at 55° C., and 1 minute at 72° C.; and one cycle consisting of 5 minutes at 72° C.

In the detection of methylation performed in this Example, each DNA fragment amplified in the DNA amplifying step is subjected to polyacrylamide gel electrophoresis to confirm the methylation state of the CpG sequences.

Figure 3:
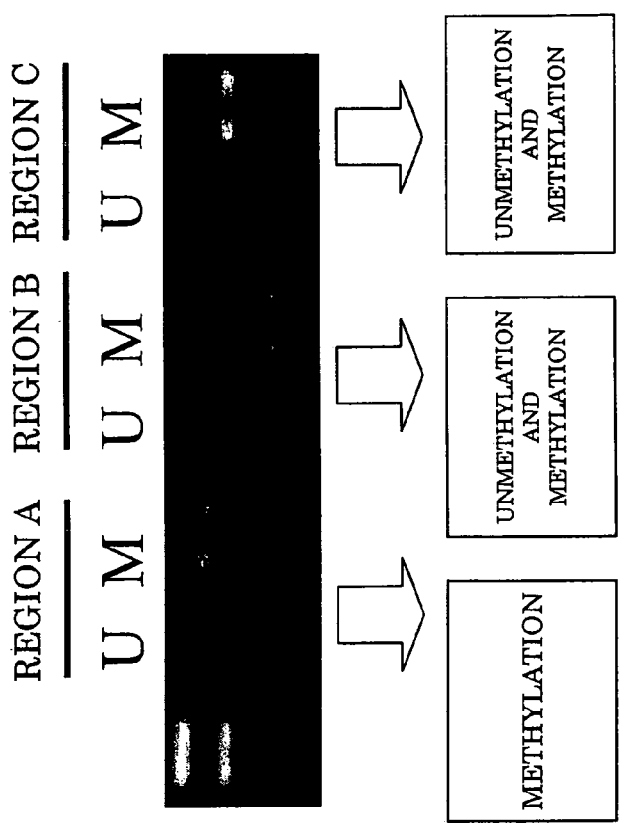
FIG. 3(a) is a diagram showing results of polyacrylamide gel electrophoresis, performed according to the MSP method described in Example, on DNA fragments that were obtained in the upstream region of DR3 gene originating in the peripheral blood lymphocytes of RA patients and amplified in a DNA amplifying step.
FIG. 3(b) is a diagram showing results of polyacrylamide gel electrophoresis, performed according to the MSP method described in Example, on DNA fragments that were obtained in the upstream region of DR3 gene originating in the synovial cells of RA patients and amplified in a DNA amplifying step.
Figure 3:
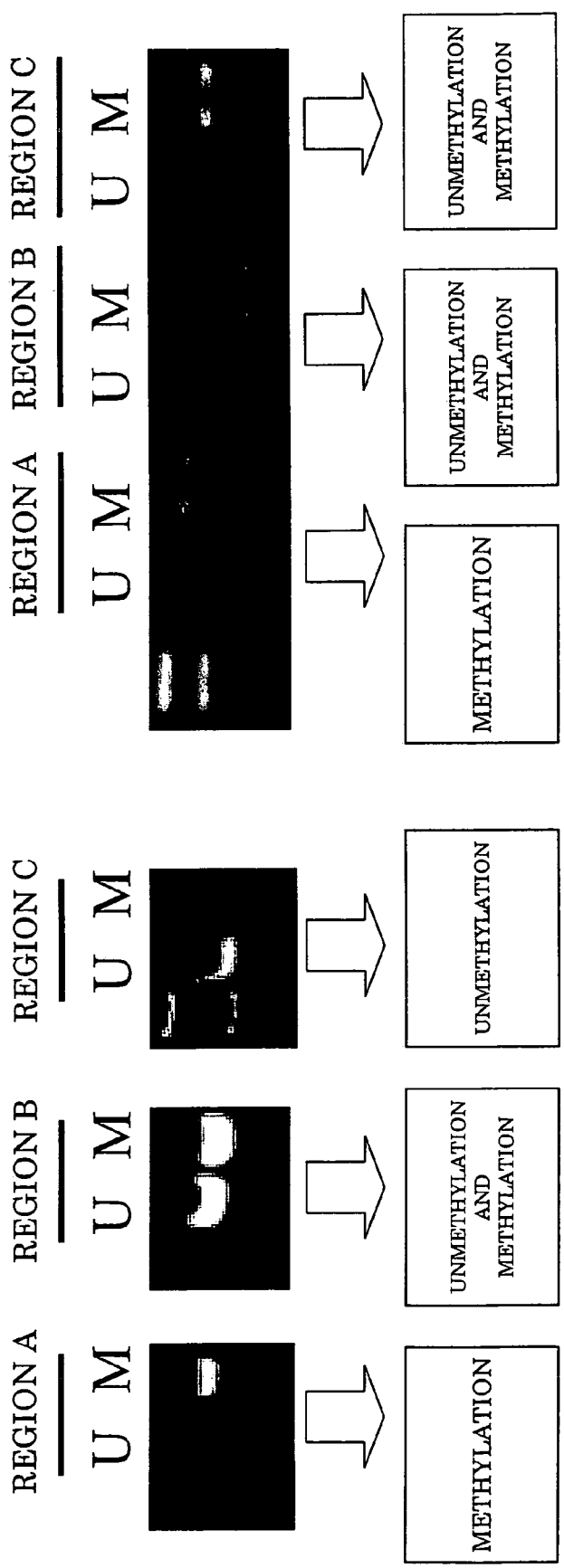
Figure 4:
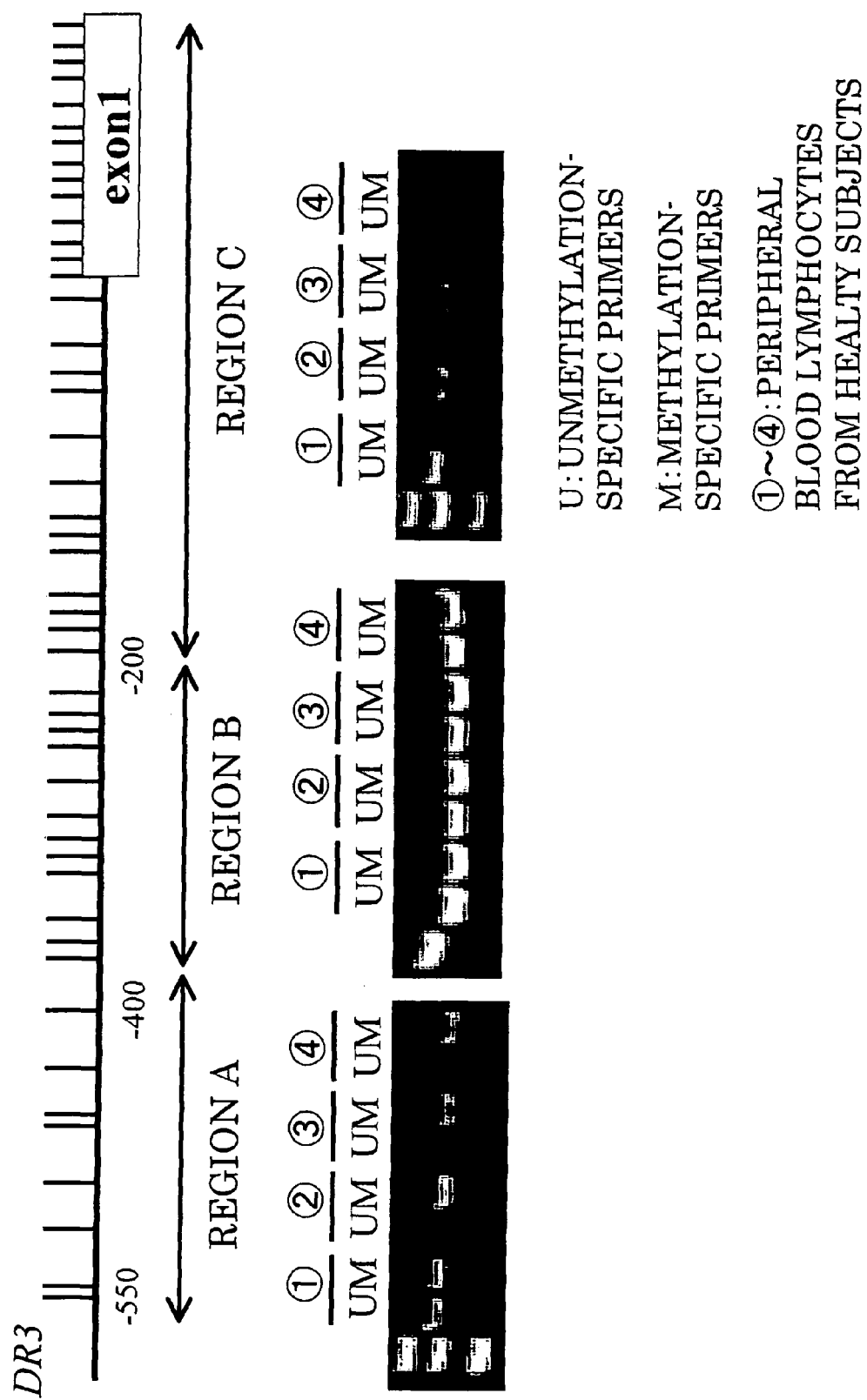
FIG. 4 is a diagram showing results of polyacrylamide gel electrophoresis, performed according to the MSP method described in Example, on DNA fragments that were obtained in the upstream region of DR3 gene originating in the peripheral blood lymphocytes of healthy subjects and amplified in a DNA amplifying step.

FIGS. 3(a) and 3(b), and FIG. 4 show the results. FIGS. 3(a) and 3(b) show the result of confirming the methylation state in A, B, and C regions, wherein FIG. 3(a) is the result for the DR3 upstream region originating in the peripheral blood lymphocytes of RA patients, and FIG. 3(b) is the result for the DR3 upstream region originating in the synovial cells of RA patients. FIG. 4 shows the result of confirming the methylation state in A, B, and C regions, with regard to the DR3 gene upstream region originating in the peripheral blood lymphocytes of healthy patients. In the results of gel electrophoresis shown in the figures, lanes under "U" indicate amplified fragments resulting from the DNA amplification performed with the unmethylation-specific primers, and lanes under "M" indicate amplified fragments resulting from the DNA amplification performed with the methylation-specific primers.

As shown in these figures, all of the CpG sequences in A region were methylated in all samples. In B region, all samples had both unmethylated and methylated CpG sequences. In C region (promoter region of DR3 gene), unmethylated and methylated CpG sequences coexisted only in samples originating in the synovial cells of RA patients, and all of the CpG sequences were unmethylated in the other samples.

These results suggest that allele-specific methylation occurs in the promoter region of DR3 gene. In RA patients, the DR3 promoter region originating in the synovial cells had a stronger methylation state than the DR3 promoter region originating in the peripheral blood lymphocytes.

The foregoing results also suggest that DR3 gene may be an imprint gene in which one of the alleles is not expressed, and that imprinting of DR3 gene is involved in the mechanism of RA development.

FIG. 5 shows results of methylation detection performed according to the foregoing method. The detection was made in the upstream region of DR3 gene in samples collected from the synovial cells, synovial cell fluid lymphocytes, and joint fluid lymphocytes of RA patients. FIG. 5(a) shows the result for A region in the DR3 gene upstream region, FIG. 5(b) shows the result for B region in the DR3 gene upstream region, and FIG. 5(c) shows the result for C region in the DR3 gene upstream region. In FIGS. 5(a) through 5(c), the numbers 1 to 3 in circles indicate gene originating in the synovial cells, gene originating in the synovial cell fluid lymphocytes, and gene originating in the joint fluid lymphocytes, respectively.

As shown in FIGS. 5(a) and 5(b), A region and B region had the same result in samples obtained from the synovial cells, synovial infiltrating lymphocytes, and lymphocytes in the joint fluid. In C region shown in FIG. 5(c), both methylation and unmethylation occurred in DR3 genes obtained from the synovial cells and synovial infiltrating lymphocytes, whereas only unmethylation was observed in DR3 gene obtained from the lymphocytes of joint fluid.

These results suggest that the methylation state in C region may be specific to the inflammation site of RA.

The number of samples was increased and the methylation state in the upstream region of DR3 gene originating in the peripheral blood lymphocytes of healthy subjects and the synovial cells of RA patients was studied again by the MSP method. The results are shown in FIG. 6. As shown in FIG. 6, the methylation state in C region differed greatly between DR3 gene originating in the peripheral blood lymphocytes of healthy subjects and the synovial cells of RA patients. In the synovial cells of osteoarthritis (OA) patients used as a control, the methylation state was weaker as compared with the synovial cells of RA patients. Due to difficulties in obtaining samples, no result was obtained for the DR3 gene originating in the synovial cells of healthy subjects. However, it is believed that the result would be similar to that of OA patients.

(2) Detection of Methylation State by Bisulfite Genomic Sequencing Method.

The methylation state in the upstream region of DR3 gene originating in the peripheral blood lymphocytes of healthy subjects and the synovial cells of RA patients was analyzed using the bisulfite genomic sequencing method. The bisulfite genomic sequencing method was performed according to the procedures described in the publication referenced above.

Figure 7:
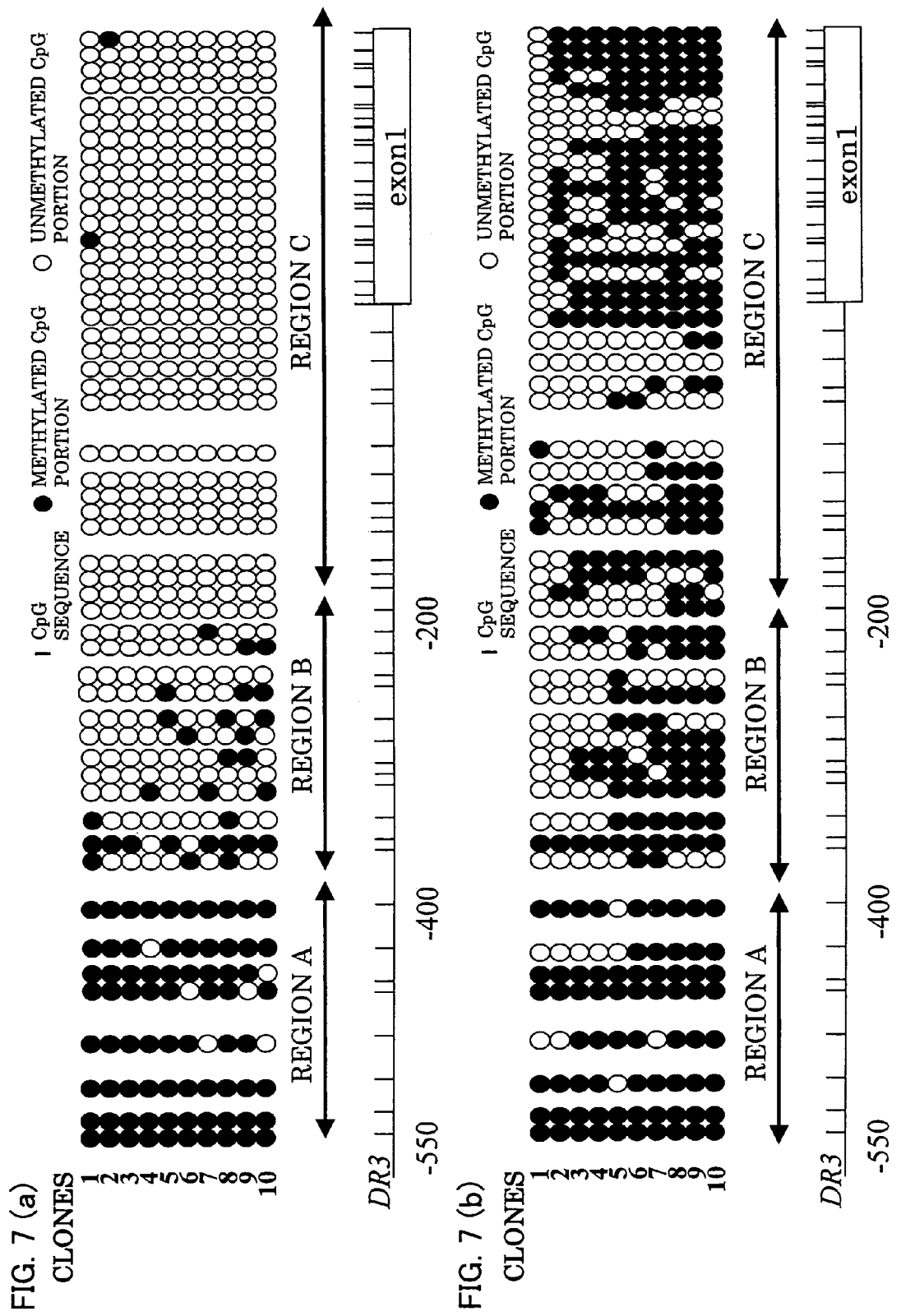
FIG. 7(a) is a diagram showing results of detection, performed according to the bisulfite genomic sequencing method described in Example, in regard to the methylation state in the upstream region of DR3 gene originating in the peripheral blood lymphocytes of healthy subjects.
FIG. 7(b) is a diagram showing results of detection, performed according to the bisulfite genomic sequencing method described in Example, in regard to the methylation state in the upstream region of DR3 gene originating in the synovial cells of RA patients.
Figure 8:
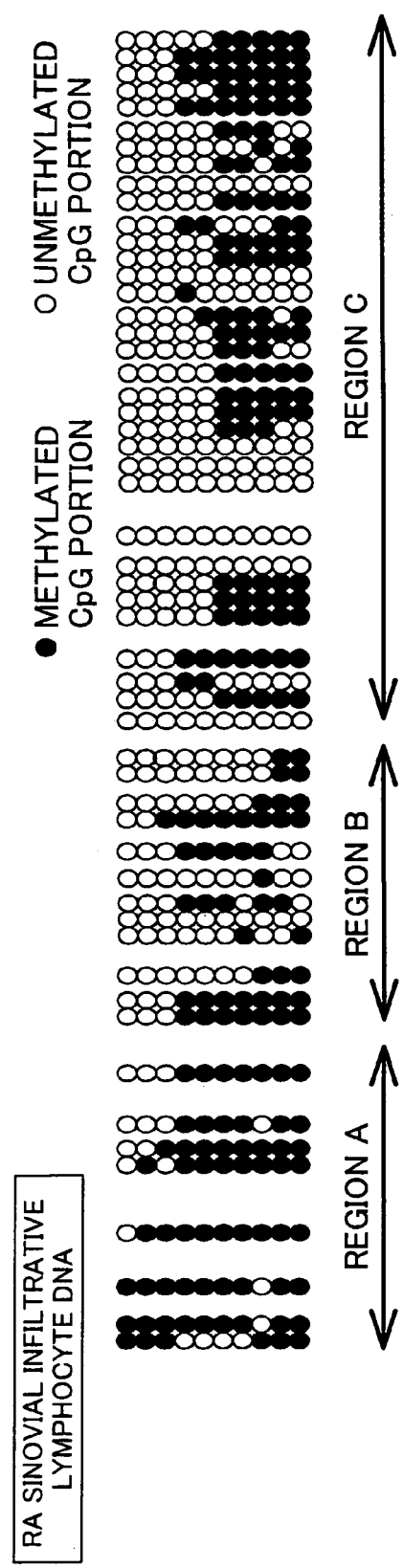
FIG. 8 is a diagram showing results of detection, performed according to the bisulfite genomic sequencing method described in Example, in regard to the methylation state in the upstream region of DR3 gene originating in the synovial infiltrating lymphocytes of RA patients.

The results are shown in FIG. 7. FIG. 7(a) shows the result of detection of methylation state in the upstream region of DR3 gene originating in the peripheral blood lymphocytes of healthy subjects. FIG. 7(b) shows the result of detection of methylation state in the upstream region of DR3 gene originating in the synovial cells of RA patients.

As shown in FIG. 7(a), the DR3 gene samples originating in the peripheral blood lymphocytes of healthy subjects showed methylation in A region, methylation and unmethylation in B region, and unmethylation in C region. The DR3 gene samples originating in the synovial cells of RA patients showed methylation in A region, methylation and unmethylation in B region, and methylation and unmethylation in C region, as shown in FIG. 7(b). These results coincide with those of the MSP method used in Section (1) above.

(3) Confirmation of DR3 Gene Expression in Synovial Cells.

Experiment was conducted to confirm expression of DR3 gene in the synovial cells of RA patients.

First, a frozen specimen and stained specimen were prepared from the synovial samples of RA patients. A tissue, approximately 5 mm$^3$ in size, was separated from the joint synovial membrane that was excised from the patient during arthroplasty. The tissue was then embedded with OTC compound, and was rapidly frozen with liquid nitrogen to obtain a frozen specimen. The frozen specimen was sliced into 6 μm sheets with Cryostat, placed on glass slides, and fixed with acetone.

The following procedures were used to establish synovial primary culture cell lines from the synovial samples of RA patients. First, the synovial membrane excised from the RA patients during arthroplasty was fragmented and subjected to collagenase treatment. The synovial cells were isolated according to ordinary method (see Hashiramoto A, Sano H, Maekawa T, et al. C-myc antisense oligodeoxynucleotides can induce apoptosis and down-regulate Fas expression in rheumatoid synoviocytes. Arthritis Rheum. 42. 954-62 (1999)). The established cell lines were maintained in 10% bovine fetal serum-supplemented Dulbecco's modified eagle medium, and were used in experiments.

(3-1) Detection of DR3 by Immunostaining

The frozen specimen of the synovial membrane of RA patients was immunostained for DR3 detection. Specifically, the frozen specimen was washed for 5 minutes with phosphate buffer, and then treated for 30 minutes with a 0.03% aqueous solution of hydrogen peroxide to eliminate inherent peroxidase activity. The specimen was washed three more times with phosphate buffer, 5 minutes each time. The subsequent steps were performed using the DAKO ENVISION+ KIT (Dako Corporation, Carpinteria, Calif., USA), according to ordinary immunostaining method (see Miyazaki S, Yoshikawa T, Hashiramoto A, et al. ACTH expression in synovium of patient with rheumatoid arthritis and Lewis rats with adjuvant arthritis. Mod Rheumatol. 12.206-212 (2002)). For the detection of DR3 protein, anti-DR3 antibody (Neo Marker, Fremont, Calif., USA) was used as the secondary antibody.

Figure 9:
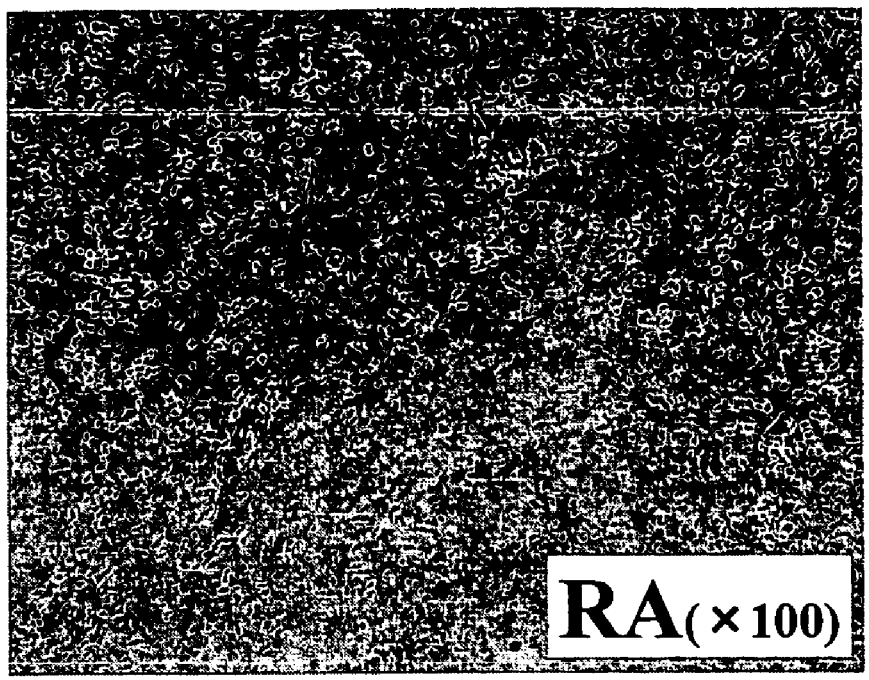
FIG. 9 is a diagram showing a result of DR3 expression as observed by immunostaining the synovial cells of RA patients.
Figure 10:
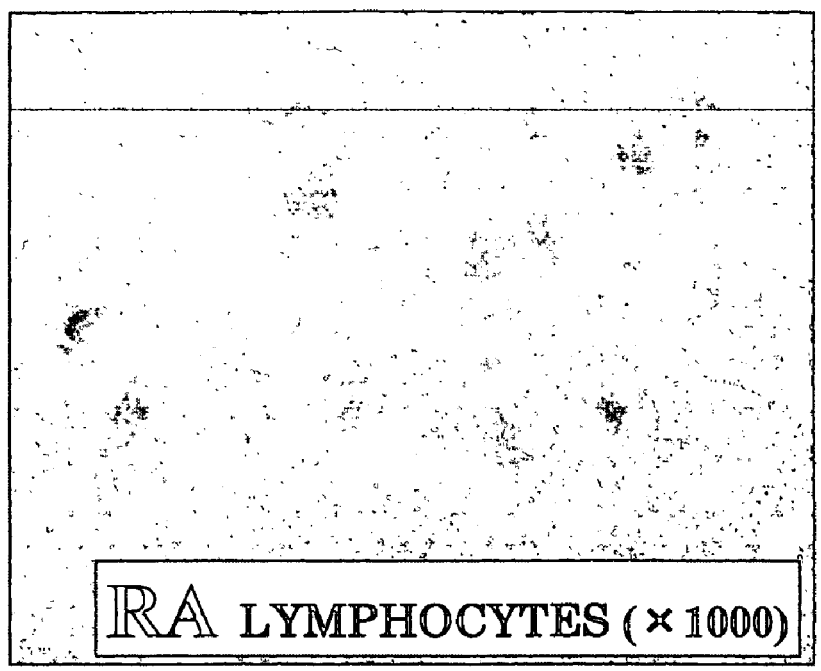
FIG. 10(a) is a diagram showing a result of DR3 expression as observed by immunostaining the synovial infiltrating lymphocytes of RA patients.
FIG. 10(b) is a diagram showing a result of DR3 expression as observed by immunostaining the synovial cells of RA patients.
Figure 10:
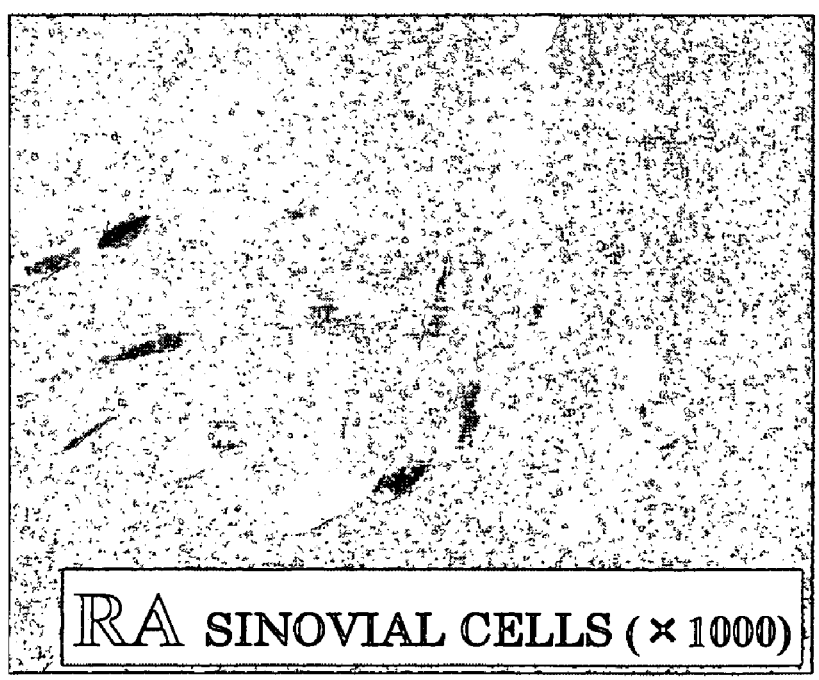

FIGS. 9 and 10 show the results. FIG. 9 is a micrograph showing the immunostained tissue at ×100 magnification in the synovial cell specimen of RA patients. FIG. 10(a) is a micrograph showing a cluster of synovial infiltrating lymphocytes at ×1000 magnification in the synovial specimen. FIG. 10(b) is a micrograph (×1000) showing a cluster of synovial cells located in the surface layer of the synovial membrane in the synovial specimen.

As shown in these Figures, the synovial cells and synovial infiltrating lymphocytes of RA patients had numerous DR3 positive cells that were stained in brown.

(3-2) Detection of DR3 by Western Blotting

Proteins were extracted from the three kinds of synovial cell lines of different origins, and DR3 proteins were detected by performing Western blotting according to ordinary method (see Yamashita T, Hashiramoto A, Haluzik M, et al. Enhanced insulin sensitivity in mice lacking ganglioside GM3. Proc Natl Acad Sci USA. 100. 3445-9.2003). As the secondary antibody, anti-DR3 antibody (eBioscience, SanDiego, Calif., USA) was used. As a positive control, Jurkat cells were used that had a high level of DR3 expression.

Figure 11:
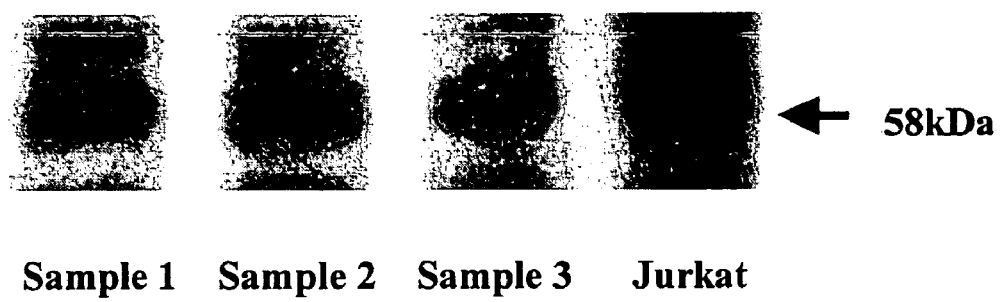
FIG. 11 is a diagram showing a result of Western blotting performed on expression of DR3 gene in the synovial cells of RA patients.

The results are shown in FIG. 11. In FIG. 11, samples 1, 2, 3, and Jurkat cells are arranged in this order from the left. Samples 1, 2, and 3 are synovial cells originating in different patients. As shown in FIG. 11, the expression of DR3 protein (58 kDa) was observed in all of samples 1, 2, and 3.

(4) Comparison of RA Patients and Osteoarthritis OA) Patients in regard to the Methylation State in DR3

By the bisulfite genomic sequencing method, a comparison was made between DR3 gene obtained from the synovial cells (SAC) of RA patients and DR3 gene obtained from the synovial cells of OA patients, in regard to the methylation state in the upstream region of DR3.

More specifically, by the bisulfite genomic sequencing method, the methylation state in the upstream region of DR3 gene was analyzed in samples obtained from the peripheral blood lymphocytes of healthy subjects and RA patients, and in samples obtained from the synovial cells of RA patients and OA patients. The bisulfite genomic sequencing method was performed according to the procedures described in the publication referenced above.

Figure 12:
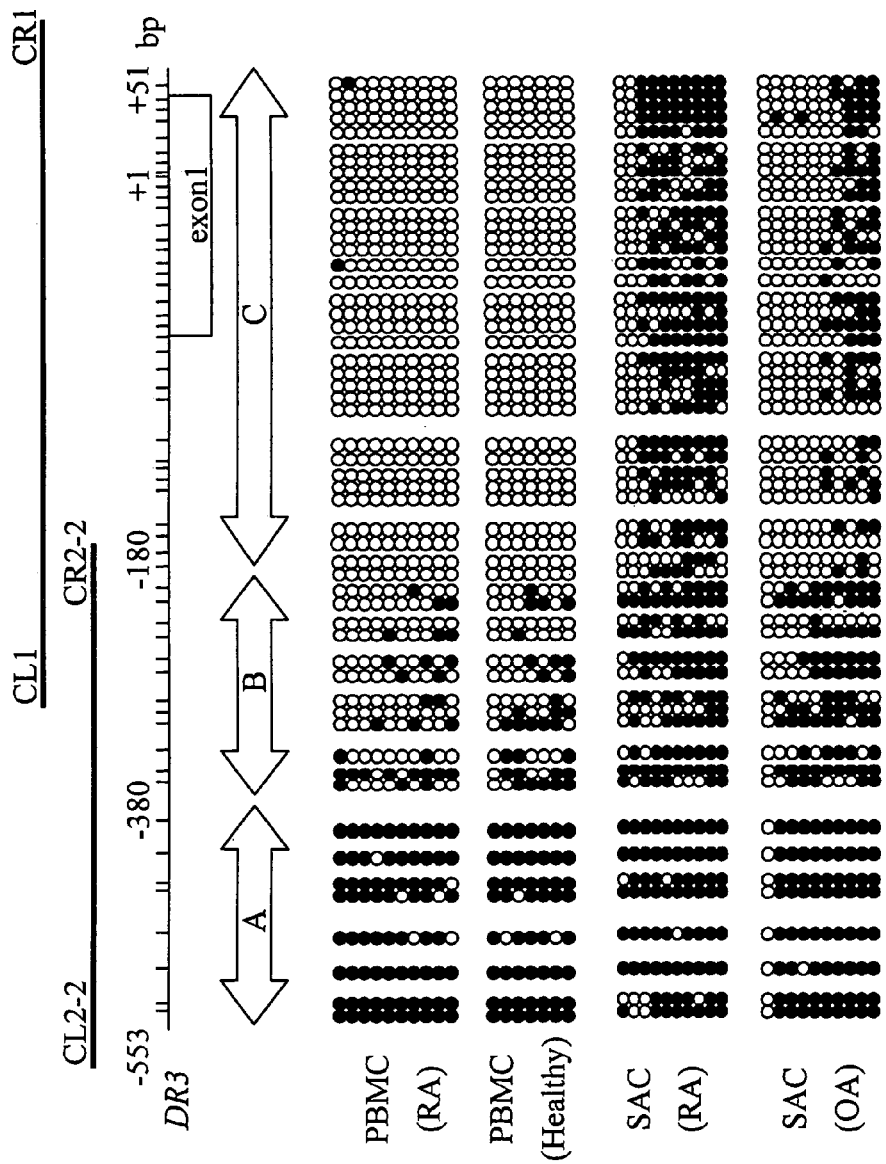
FIG. 12 is a diagram showing results of detection, performed according to the bisulfite genomic sequencing method described in Example, in regard to the methylation state in the upstream region of DR3 originating in the peripheral blood lymphocytes of healthy subjects and RA patients and in the synovial cells of osteoarthritis (OA) patients.

The results are shown in FIG. 12. The results shown in FIG. 12 include results of analysis on the methylation state in the upstream region of DR3 gene in samples obtained from the peripheral blood lymphocytes (PBMC) of healthy subjects and RA patients. The analysis on the upstream region of DR3 gene obtained from the peripheral blood lymphocytes (PBMC) of healthy subjects and RA patients yielded the same results as above: strong methylation state in A region, methylation and unmethylation states in B region, and complete unmethylation state in C region. CL1/CR1 and CL2-2/CR2-2 shown in the upper portion of FIG. 12 are primers used in this experiment.

In the upstream region of DR3 gene obtained from the synovial cells (SAC), samples obtained from RA patients showed strong methylation state, whereas samples obtained from OA patients tended to show a reduced level of methylation.

Figure 13:
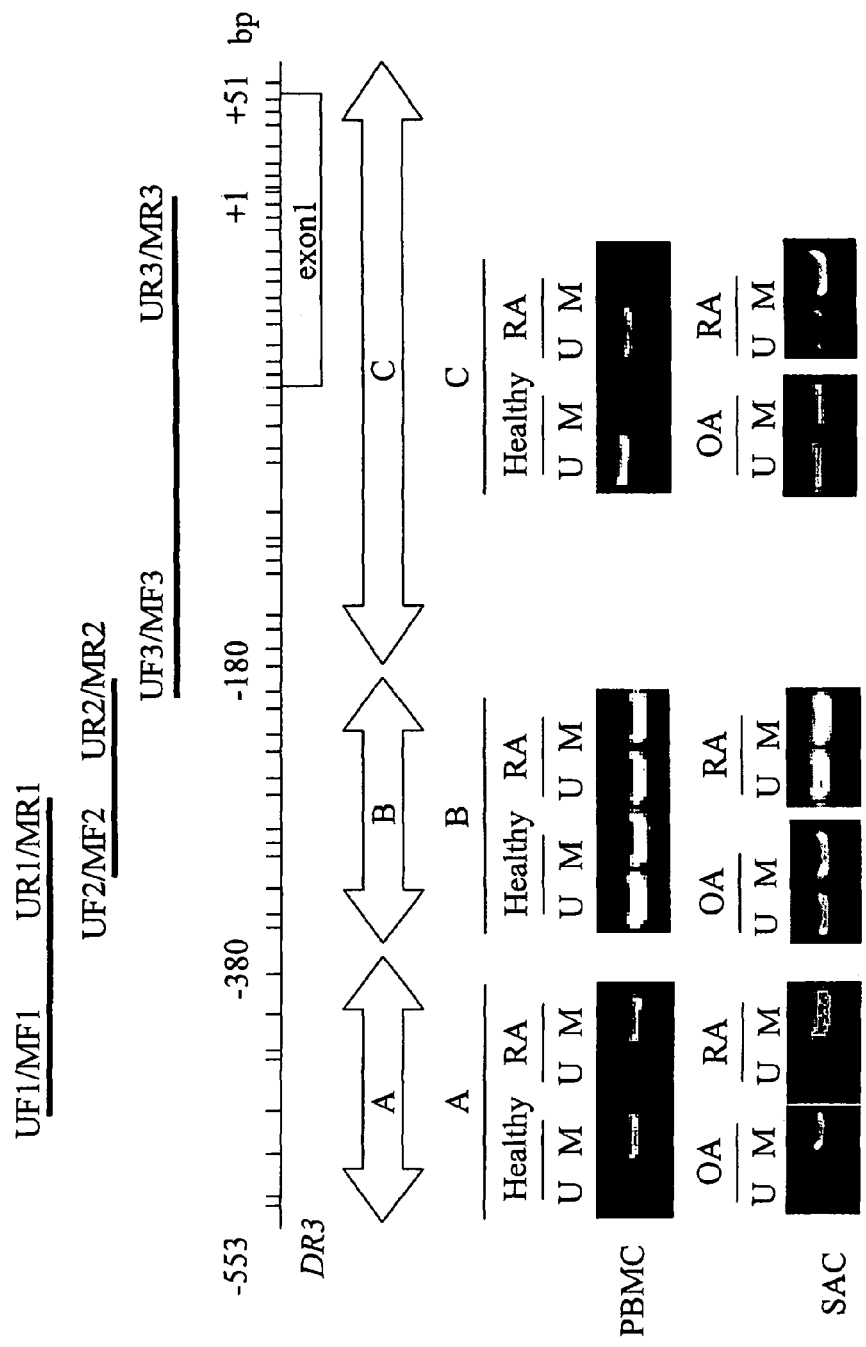
FIG. 13 is a diagram showing results of polyacrylamide gel electrophoresis, performed according to the MSP method described in Example, on DNA fragments that were obtained from the upstream region of DR3 gene and amplified in a DNA amplifying step, and also showing results of detection that was performed in regard to the methylation state in the upstream region of DR3 originating in the peripheral blood lymphocytes of healthy subjects and RA patients and in the synovial cells of osteoarthritis (OA) patients.

Detection of methylation state was also made for the same gene, using the MSP method. The results are shown in FIG. 13. MF1/MR1, MF2/MR2, and MF3/MR3 are methylation-specific primers used in this experiment. UF1/UR1, UF2/UR2, and UF3/UR3 are unmethylation-specific primers used in this experiment. As shown in FIG. 13, the experiment by the MSP method yielded the same results as those obtained by the bisulfite genomic sequencing method.

It was found from these results that C region of DR3 gene originating in the synovial cells had a strong methylation state particularly in RA patients.

More specifically, FIG. 13 shows the results, confirming the state of methylation in A, B, and C regions in the upstream region of DR3 gene in samples originating in the peripheral blood lymphocytes of healthy subjects and RA patients, and in samples originating in the synovial cells of RA patients and OA patients. In the results of gel electrophoresis shown in FIG. 13, lanes under "U" indicate amplified fragments resulting from the DNA amplification performed with the unmethylation-specific primers, and lanes under "M" indicate amplified fragments resulting from the DNA amplification performed with the methylation-specific primers. MF1/MR1, MF2/MR2, and MF3/MR3 are methylation-specific primers used in this experiment. UF1/UR1, UF2/UR2, and UF3/UR3 are unmethylation-specific primers used in this experiment.

As shown in FIG. 13, all samples had the CpG sequences methylated in A region. In B region, all samples had both methylated and unmethylated CpG sequences. In C region (promoter region of DR3 gene), methylation was particularly strong in the synovial cells of RA patients.

(5) Confirmation of DR3 Promoter Activity Using Luciferase Assay.

Figure 14:
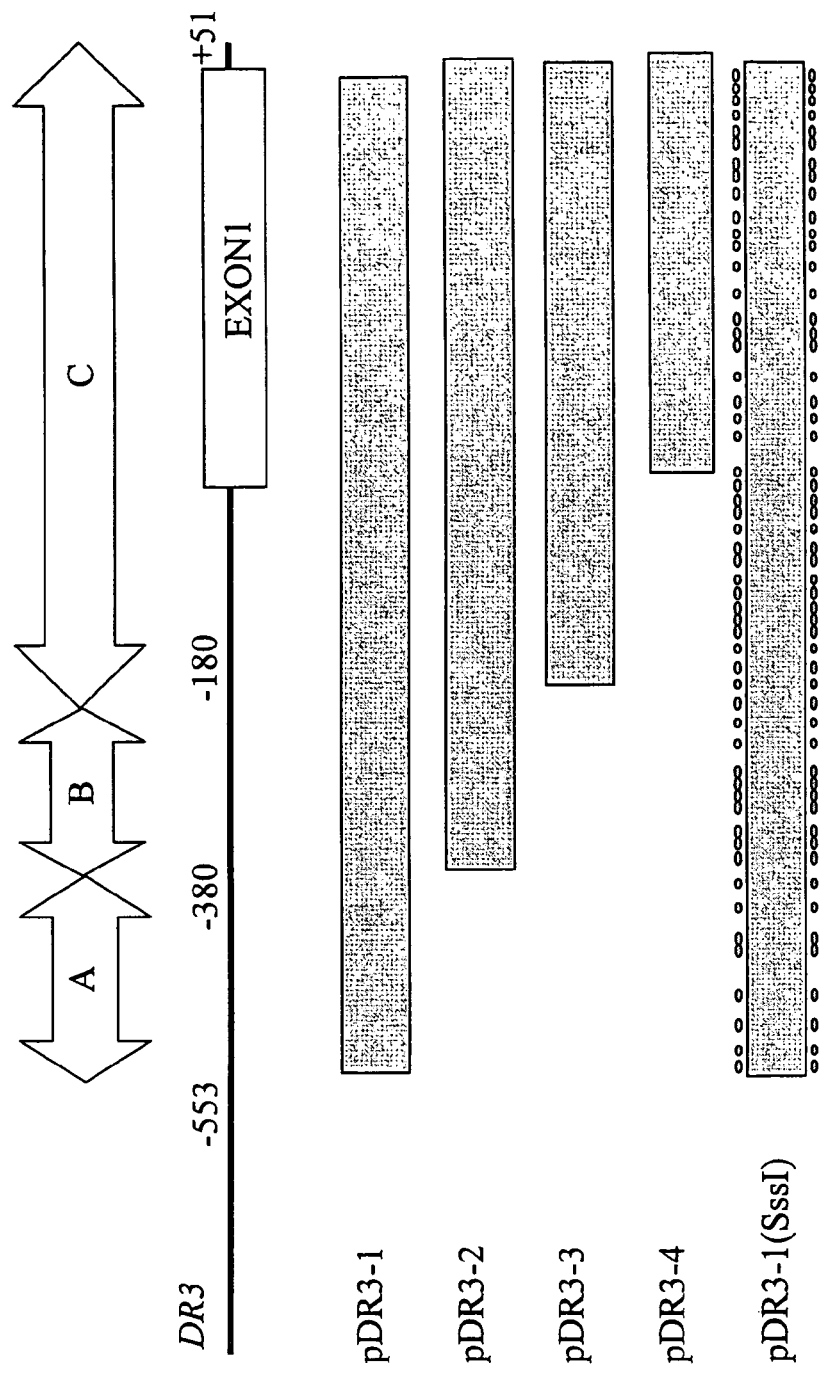
FIG. 14 is a diagram schematically showing inserts (pDR3-1 through pDR3-4, and pDR3-1 (SssI)) respectively inserted into constructed plasmids.

Four kinds of inserts (pDR3-1 through pDR3-4) originating in peripheral blood lymphocyte DNA of healthy patients were inserted into pGL3-Enhancer vector (Promega), so as to construct reporter plasmids respectively containing these inserts. In addition, plasmid pDR3-1 (SssI) was constructed that was artificially methylated with the use of CpG methylase SssI (New England Biolabs). FIG. 14 schematically illustrates the inserts, pDR3-1 through pDR3-4, and pDR3-1 (SssI), that were inserted into the plasmids constructed in this example. As shown in FIG. 14, pDR3-1 and pDR3-1 (SssI) included A, B, and C regions (including exon 1) of DR3 gene, pDR3-2 included B and C regions (including exon 1) of DR3 gene, pDR3-3 included only C region (including exon 1) of DR3 gene, and pDR3-4 included only exon 1 of DR3 gene.

On the day before the transfection with these plasmids, COS-7 was inoculated on a 24-well plate ($1\times10^5$ cell/well). On the next day, COS-7 was transfected with the reporter plasmids using Lipofect AMINE with PLUS (Invitrogen). After adjusting reagents and samples, the luciferase activity of each plasmid was measured with a luminometer, Dual-Luciferase Reporter Assay System Kit (Promega).

Figure 15:
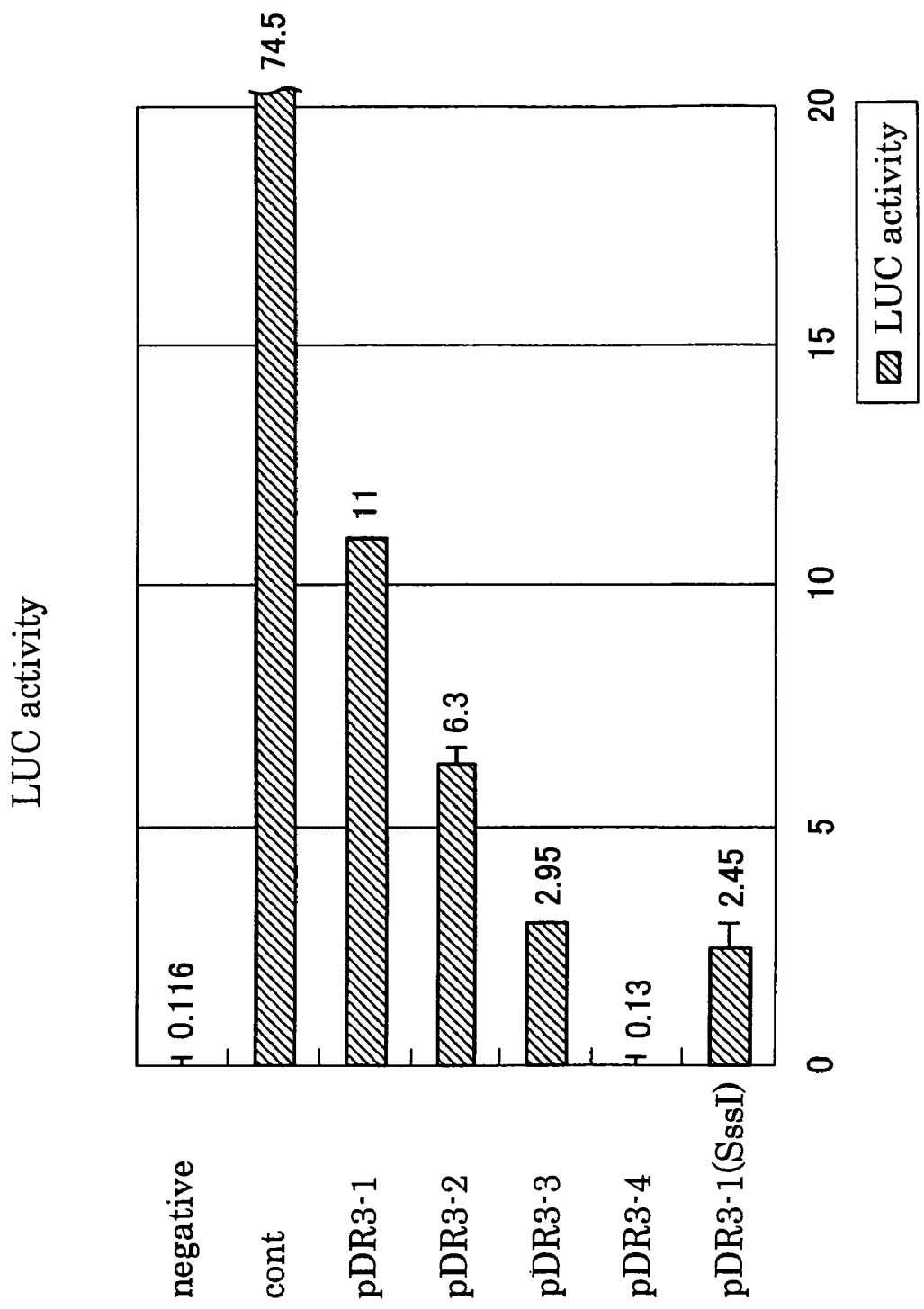
FIG. 15 is a graph showing a result of measurement on relative luciferase activity in the plasmids that have incorporated the inserts shown in FIG. 14.

FIG. 15 shoes the resulting relative luciferase activity. As shown in FIG. 15, the relative luciferase activity decreased as the length of DR3 promoter region inserted into the vector decreased from pDR3-1 to pDR3-4. It was also found that the methylated plasmid had reduced luciferase activity as compared with the unmethylated plasmids, even though the methylated plasmid contained all of the A, B, and C regions.

These results suggest that the methylation has the suppressing action on the expression of DR3 gene in its promoter region. That is, it is conceivable that the expression of DR3 gene is suppressed in the synovial cells of RA patients whose promoter region is methylated relatively strongly, and that this is associated with the development of RA.

(6) Relation between Expression of DR3 Protein and Methylation State of DR3 Gene.

Figure 16:
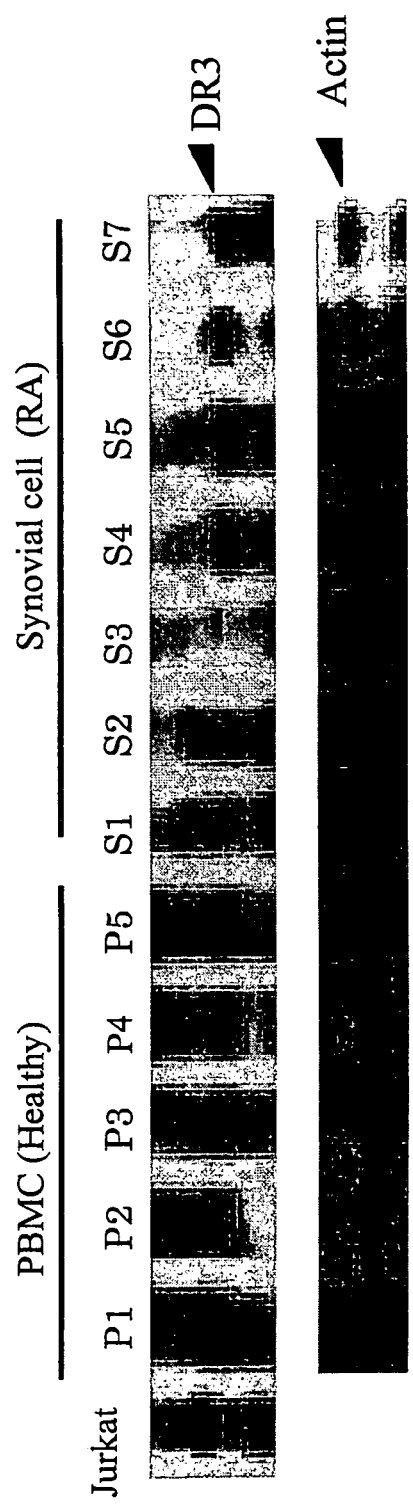
FIG. 16(a) is a diagram showing a possible relation between DR3 protein expression and DR3 methylation state (C region), which are results of investigation on protein expression performed by Western blotting.
FIG. 16(b) is a diagram showing a possible relation between DR3 protein expression and DR3 methylation state (C region), which are results of methylation analysis by the MSP method.
Figure 16:
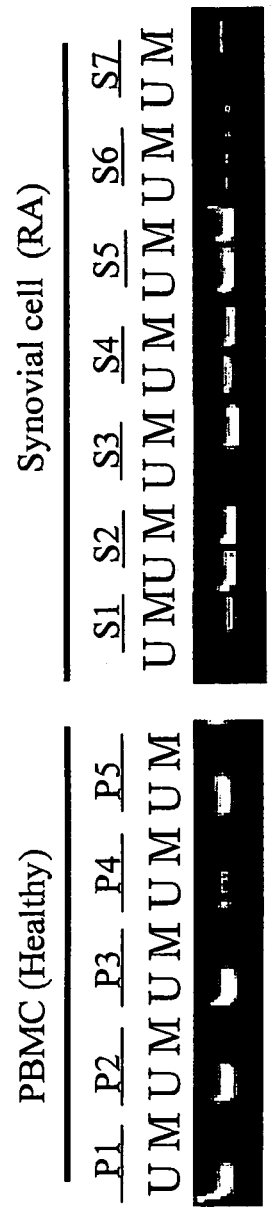

In this example, the expression of DR3 protein in the peripheral blood lymphocytes of healthy subjects and the synovial cells of RA patients was confirmed by Western blotting method according to the procedure described in Section (3-2) above. The methylation state in the promoter region of DR3 gene was also confirmed for the same specimens, using the MSP method. The results are shown in FIG. 16. FIG. 16(a) shows the result of Western blotting method on protein expression. FIG. 16(b) shows the result of methylation analysis performed by the MSP method on C region. In FIGS. 16(a) and 16(b), "PBMC (P1 through P5)" are specimens obtained from the peripheral blood lymphocytes of healthy subjects, and "synovial cells (S1 through S7)" are specimens obtained from the synovial cells of RA patients. In FIG. 16(b), "U" denotes unmethylation, and "M" denotes methylation.

As shown in the upper portion of FIG. 16(a), the synovial cells originating in RA patients had thinner DR3 protein bands than the peripheral blood lymphocytes originating in healthy subjects. It was therefore found from the result that the expression level of DR3 protein had been reduced in the synovial cells of RA patients more so than in the peripheral blood lymphocytes of healthy subjects. The result of Western blotting shown in the lower portion of FIG. 16(a) is the result for actin protein used as a control. The result showed that the expression level of actin protein was no different between healthy subjects and RA patients.

Further, as shown in FIG. 16(b), the peripheral blood lymphocytes of healthy subjects on the left-hand side of the Figure showed no methylation at all, whereas the synovial cells of RA patients on the right-hand side of the Figure had a stronger methylation state as compared with the healthy subjects. Specimens S3 and S7, which were found by the MSP method to be completely methylated (see FIG. 16(b)) showed particularly low levels of DR3 protein expression (see FIG. 16(a)).

It was therefore confirmed by these results that the synovial cells of RA patients showing a strong methylation state in the promoter region of DR3 gene had a reduced expression level of DR3 protein, which is the actual translation product of DR3 gene. The results therefore suggest that the expression of DR3 protein is suppressed in the synovial cells of RA patients whose promoter region is methylated relatively strongly, and that this is associated with the development of RA.

The results of this example therefore confirmed that it would be indeed possible to determine development of RA or the likelihood of developing RA, if, using DR3 gene originating in the peripheral blood lymphocytes of healthy subjects as a control, the DR3 promoter region obtained from the synovial cells or synovial infiltrating lymphocytes of the subject was more strongly methylated than the DR3 promoter region originating in the above peripheral blood lymphocytes.

As described above, it was confirmed that DR3 gene is expressed in the synovial cells and synovial infiltrating lymphocytes of RA patients. This suggested the possibility that DR3 gene might be involved in the pathology of RA. Further, from the fact that expression of DR3 gene was confirmed in the synovial tissues of RA patients, it is believed that differences in the methylation state of the DR3 promoter region considered as the gist of the present invention, are associated with the expression of DR3 gene in the synovial tissues and therefore development of RA.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A polynucleotide according to the present invention can advantageously be used to elucidate the mechanism of human RA development. Further, a polynucleotide according to the present invention is useful for the diagnosis of RA and the determination of likelihood of RA development. A polynucleotide according to the present invention can also be used as a medicament for treating RA.

With a kit and method for diagnosis of RA according to the present invention, it is possible to accurately and conveniently determine whether a subject has developed RA or has the likelihood of developing RA. The present invention is therefore useful for the prevention and treatment of RA.

A polynucleotide according to the present invention can therefore advantageously be used to elucidate the mechanism of RA development. With the present invention, whether a subject has developed RA or has the likelihood of developing RA can be determined both accurately and conveniently. The present invention is therefore potentially very useful in the treatment and prevention of RA.

The invention claimed is:

1. A method for determining whether a human subject has developed rheumatoid arthritis or has the likelihood of developing rheumatoid arthritis, comprising:
   (i) detecting whether CpG sequences in a region from base 374 to base 592 of SEQ ID NO: 1 in a DR3 gene promoter region obtained from synovial cells or synovial infiltrating lymphocytes of the human subject are methylated or not; and
   (ii) determining that the human subject has developed rheumatoid arthritis or has the likelihood of developing rheumatoid arthritis when there is an increase in the number of methylated CpG sequences in the region from base 374 to base 592 of SEQ ID NO: 1 are methylated as compared to a control DR3 gene promoter region from base 374 to base 592 of SEQ ID NO: 1.

2. A method as set forth in claim 1, wherein (i) comprises:
   a DNA converting step of converting unmethylated cytosines to uracils in CpG sequences contained in the DR3 gene promoter region obtained from the synovial cells or synovial infiltrating lymphocytes by treating the DR3 gene promoter region with a bisulfite-containing reagent;
   a DNA amplifying step of amplifying the DR3 gene promoter region, after the treatment in the DNA converting step, by a polymerase chain reaction using methylation-specific primers or unmethylation-specific primers;
   a methylation-state detecting step of detecting how many CpG sequences are methylated, by detecting whether the polymerase chain reaction in the DNA amplifying step using the methylation-specific primers or the unmethylation-specific primers has amplified the DR3 gene promoter region; and
   a comparing step of comparing the DR3 gene promoter region obtained from the synovial cells or synovial infiltrating lymphocytes with the DR3 gene promoter region obtained from the peripheral blood lymphocytes, in regard to the methylation state of the DR3 gene promoter regions detected in the methylation-state detecting step, or a confirming step of confirming that the DR3 promoter region obtained from the synovial cells or synovial infiltrating lymphocytes is strongly methylated.

3. A method for determining whether a human subject has developed rheumatoid arthritis or has a likelihood of developing rheumatoid arthritis, comprising:
   detecting whether CpG sequences from base 374 to base 592 of SEQ ID NO: 1 in a DR3 gene promoter region obtained from synovial cells or synovial infiltrating lymphocytes of a human subject are methylated or not;
   detecting whether CpG sequences from base 374 to base 592 of SEQ ID NO: 1 in a DR3 gene promoter region obtained from peripheral blood lymphocytes of the human subject are methylated or not;
   comparing methylation of the DR3 gene promoter region obtained from the synovial cells or synovial infiltrating lymphocytes with methylation of the DR3 gene promoter region obtained from the peripheral blood lymphocytes; and
   determining that the human subject has developed rheumatoid arthritis or has the likelihood of developing rheumatoid arthritis when the DR3 gene promoter region obtained from the synovial cells or synovial infiltrating lymphocytes is methylated at a higher ratio than the DR3 gene promoter region obtained from the peripheral blood lymphocytes.

4. A method for determining whether a human subject has developed rheumatoid arthritis or has a likelihood of developing rheumatoid arthritis, comprising:
   detecting whether CpG sequences from base 374 to base 592 of SEQ ID NO: 1 in a DR3 gene promoter region obtained from synovial cells or synovial infiltrating lymphocytes of a human subject are methylated or not;
   comparing methylation of the DR3 gene promoter region obtained from the synovial cells or synovial infiltrating lymphocytes with a control DR3 gene promoter region obtained from peripheral blood lymphocytes of a healthy human subject; and determining that the human subject has developed rheumatoid arthritis or has the likelihood of developing rheumatoid arthritis when the DR3 gene promoter region obtained from the synovial cells or synovial infiltrating lymphocytes is methylated at a higher ratio than the DR3 gene promoter region originating in the peripheral blood lymphocytes of the healthy human subject.

5. A method as set forth in claim 2, wherein the methylation-specific primers and the unmethylation-specific primers are designed to amplify at least the nucleotide sequence from base 374 to base 564 of SEQ ID NO: 1.

6. A method as set forth in claim 2, wherein:
the methylation-specific primers consist of SEQ ID NOS: 2 and 3, respectively, and
the unmethylation-specific primers consist of SEQ ID NOS: 4 and 5, respectively.

\* \* \* \* \*